United States Patent [19]

Debono

[11] 4,396,543
[45] Aug. 2, 1983

[54] DERIVATIVES OF A-21978C CYCLIC PEPTIDES

[75] Inventor: Manuel Debono, Indianapolis, Ind.

[73] Assignee: Eli Lilly and Company, Indianapolis, Ind.

[21] Appl. No.: 380,499

[22] Filed: May 21, 1982

[51] Int. Cl.³ .......................................... C07C 103/52
[52] U.S. Cl. .............................................. 260/112.5 R
[58] Field of Search ................................. 260/112.5 R

[56] References Cited

U.S. PATENT DOCUMENTS

| | | | |
|---|---|---|---|
| 3,150,059 | 9/1964 | Kleinschmidt et al. | 260/112.5 R |
| 4,050,989 | 9/1977 | Kuwana et al. | 260/112.5 R |
| 4,208,403 | 6/1980 | Hamill et al. | 424/115 |
| 4,293,482 | 10/1981 | Abbott et al. | 260/112.5 R |
| 4,293,483 | 10/1981 | Debono | 260/112.5 R |
| 4,293,485 | 10/1981 | Debono | 260/112.5 R |
| 4,293,487 | 10/1981 | Debono | 260/112.5 R |
| 4,293,488 | 10/1981 | Debono | 260/112.5 R |
| 4,293,491 | 10/1981 | Debono | 260/112.5 R |

FOREIGN PATENT DOCUMENTS 38-405867  7/1963  Japan ............................ 260/112.5 R

OTHER PUBLICATIONS

T. Kato et al., *J. Antibiotics* 29, (12), 1339–1340, (1976).
S. Chihara et al., *Agr. Biol. Chem.* 37, (11), 2455–2463, (1973).
S. Chihara et al., *ibid.* 37, (12), 2709–2717, (1973).
S. Chihara et al., *ibid.* 38, (3), 521–529, (1974).
S. Chihara et al., *ibid.* 38, (10), 1767–1777, (1974).
T. Suzuki et al., *J. Biochem.* 56, (4), 335–343, (1964).
J. M. Weber et al., *J. Antibiotics* 31, (4), 373–374, (1978).
J. Shoji et al., *ibid.* 28, 764–769, (1975).
J. Shoji et al., *ibid.* 29, (4) 380–389, (1976).
J. Shoji et al., *ibid.* 29, (12), 1268–1274, (1976).
J. Shoji et al., *ibid.* 29, (12), 1275–1280, (1976).

*Primary Examiner*—Delbert R. Phillips
*Attorney, Agent, or Firm*—Nancy J. Harrison; Arthur R. Whale

[57] ABSTRACT

A-21978C cyclic peptide derivatives of the formula

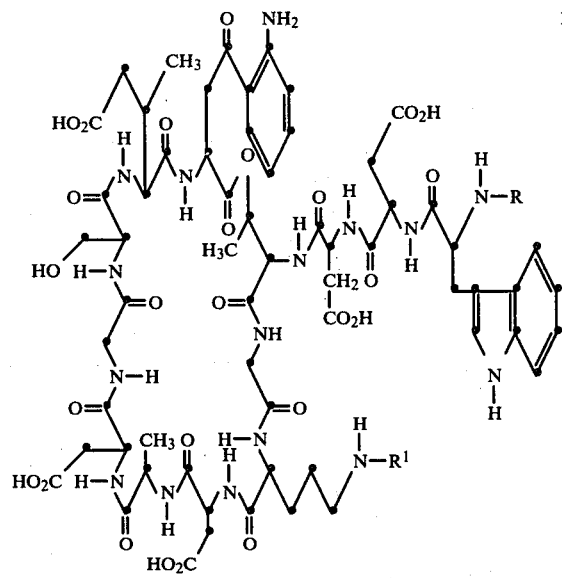

wherein R is hydrogen, a specified aminoacyl or N-alkanoylaminoacyl group, 8-methyldecanoyl, 10-methyldodecanoyl, 10-methylundecanoyl, the specific $C_{10}$-alkanoyl group of A-21978$C_0$ or the specific $C_{12}$-alkanoyl groups of A-21978C factors $C_4$ and $C_5$ or an amino-protecting group; and $R^1$ is hydrogen, an amino-protecting group, or a specified aminoacyl or N-alkanoylaminoacyl group; provided that, when R is other than aminoacyl or N-alkanoylaminoacyl, $R^1$ must be aminoacyl or N-alkanoylaminoacyl; and, when $R^1$ is an amino-protecting group, R must be aminoacyl or N-alkanoylaminoacyl; and the salts thereof, are useful as antibacterial agents or as intermediates to antibacterial agents.

34 Claims, No Drawings

DERIVATIVES OF A-21978C CYCLIC PEPTIDES

SUMMARY OF THE INVENTION

This invention relates to derivatives of A-21978C cyclic peptides which have formula 1:

wherein R is hydrogen, a specified aminoacyl or N-alkanoylaminoacyl group, 8-methyldecanoyl, 10-methylundecanoyl, 10-methyldodecanoyl, the specific $C_{10}$-alkanoyl group of A-21978C factor $C_0$ or the specific $C_{12}$-alkanoyl groups of A-21978C factors $C_4$ and $C_5$ or an amino-protecting group; and $R^1$ is hydrogen, a specified aminoacyl or N-alkanoylaminoacyl group or an amino-protecting group; provided that, when R is other than aminoacyl or N-alkanoylaminoacyl, $R^1$ must be aminoacyl or N-alkanoylaminoacyl; and, when $R^1$ is an amino-protecting group, R must be aminoacyl or N-alkanoylaminoacyl; and the salts of these peptides. The A-21978C cyclic peptide derivatives and salts of this invention are useful semi-synthetic antibacterial agents or are useful as intermediates to such agents.

DETAILED DESCRIPTION OF THE INVENTION

In this specification the following abbreviations, most of which are commonly known in the art, are used:
Ala: alanine
Asp: aspartic acid
Gly: glycine
Kyn: kynurenine
Orn: ornithine
Ser: serine
Thr: threonine
Trp: tryptophan
t-BOC: tert-butoxycarbonyl
Cbz: benzyloxycarbonyl
DMF: dimethylformamide
THF: tetrahydrofuran
HPLC: high performance liquid chromatography
NMR: $^1$H nuclear magnetic resonance
TLC: thin-layer chromatography
UV: ultraviolet

FIELD OF THE INVENTION

Although there are many known antibacterial agents, the need for improved antibiotics continues. Antibiotics differ in their effectiveness against pathogenic organisms. Organism strains which are resistant to known antibiotics continually develop. In addition, individual patients often suffer serious reactions to specific antibiotics, due to hypersensitivity and/or to toxic effects. There is, therefore, a continuing need for new and improved antibiotics.

THE PRIOR ART

The A-21978C antibiotics are closely related, acidic peptide antibiotics. Members of this class of antibiotics which were previously known include crystallomycin, amphomycin, zaomycin, aspartocin, and glumamycin [see T. Korzybski, Z. Kowszyk-Gindifer and W. Kurylowicz, "Antibiotics-Origin, Nature and Properties," Vol. I, Pergamon Press, New York, N.Y., 1967, pp. 397–401 and 404–408]; tsushimycin [J. Shoji, et al., *J. Antibiotics* 21, 439–443 (1968)]; laspartomycin [H. Naganawa, et al., *J. Antibiotics* 21, 55–62 (1968)]; brevistin [J. Shoji and T. Kato, *J. Antibiotics* 29, 380–389 (1976)]; cerexin A [J. Shoji, et al., *J. Antibiotics* 29, 1268–1274 (1976)] and cerexin B [J. Shoji and T. Kato, *J. Antibiotics* 29, 1275–1280 (1976)]. Of these antibiotics, brevistin, cerexin A and cerexin B appear to be most closely related to the A-21978C antibiotics.

The A-21978C antibiotics are described by Robert L. Hamill and Marvin M. Hoehn in U.S. Pat. No. 4,208,403, issued June 17, 1980, which is incorporated herein by reference. As described in U.S. Pat. No. 4,208,403, the A-21978 antibiotic complex contains a major component, factor C, which is itself a complex of closely related factors. A-21978 factor C, which is called the A-21978C complex, contains individual factors $C_0$, $C_1$, $C_2$, $C_3$, $C_4$ and $C_5$. Factors $C_1$, $C_2$ and $C_3$ are major factors; and factors $C_0$, $C_4$ and $C_5$ are minor factors. The structure of the A-21978C factors is shown in formula 2:

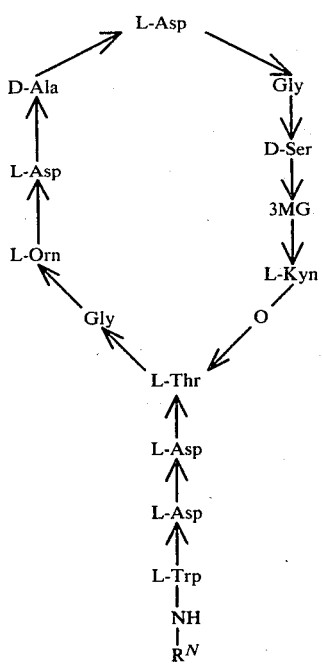

wherein 3MG represents L-threo-3-methylglutamic acid, and $R^N$ represents a specific fatty acid moiety. The specific $R^N$ groups of the factors are as follows:

| A-21978C Factor | $R^N$ Moiety |
|---|---|
| $C_1$ | 8-methyldecanoyl |
| $C_2$ | 10-methylundecanoyl |
| $C_3$ | 10-methyldodecanoyl |
| $C_0$ | $C_{10}$-alkanoyl* |
| $C_4$ | $C_{12}$-alkanoyl* |
| $C_5$ | $C_{12}$-alkanoyl* |

*Identity not yet determined

Kleinschmidt et al. in U.S. Pat. No. 3,150,059, issued in 1964, described an enzyme elaborated by the Actinoplanaceae which was capable of deacylating penicillin antibiotics. Abbott and Fukuda in U.S. Pat. No. 4,293,482, issued in 1981, reported that an Actinoplanaceae enzyme was capable of deacylating the A-30912 type of cyclic peptide antibiotic.

In 1967 Kimura and Tatsuki, in Japanese Patent No. 4058/67 (Derwent Abstr. 26695), described the enzymatic deacylation of the peptide antibiotic glumamycin. The microorganism catalyzing the deacylation was identified as closely related to Pseudomonas dacunhae. They stated that "deacylated derivatives of the compounds are useful as the material for synthesis of the related compounds, as in the case of 6-aminopenicillanic acid for penicillin", but gave no examples of re-acylation.

In 1965, Kimura and coworkers reported that a bacterium isolated from soil catalyzed the deacylation of the peptide antibiotic colistin (polymyxin E) (see Kimura, et al., Abstracts of Papers, 21st Meeting of the Pharmaceutical Society of Japan, Tokushima, October, 1965, p. 422). They reported that new derivatives of colistin were prepared by acylation of the deacylated nucleus, but did not discuss whether these derivatives had any activity.

Kato and Shoji [J. Antibiotics 29 (12), 1339-1340 (1976)] attempted to use the enzyme described by Kimura et al. to deacylate the cyclic peptide antibiotic octapeptin $C_1$. The enzyme did not catalyze the desired reaction. It was subsequently found that deacylation could be accomplished chemically by oxidation of the $\beta$-hydroxyl group of the fatty acid followed by treatment with hydroxylamine.

In 1973 Chihara and coworkers reported their work with colistin. In this work two plant proteases, ficin and papain, were used to hydrolyze colistin to a nonapeptide and a fatty acyl $\alpha,\gamma$-diaminobutyric acid residue. The plant enzymes, however, in addition to removing the fatty acid acyl substituent, also removed the terminal amino acid of the colistin molecule [See S. Chihara et al., Agr. Biol. Chem. 37 (11), 2455-2463 (1973); ibid. 37 (12), 2709-2717 (1973); ibid. 38 (3), 521-529 (1974); and ibid. 38 (10), 1767-1777 (1974)]. The colistin nonapeptide was isolated and then reacylated with a variety of fatty acid chlorides. Subsequently, Chihara's group produced N-fatty acyl monoacyl derivatives of colistin nonapeptide. These derivatives restored a tenth amino acid to the colistin nonapeptide and were used to study structure-activity relationships.

The polymyxin antibiotics have been hydrolyzed with the enzyme subtilopeptidase A [See T. Suzuki et al., J. Biochem. 56 (4), 335-343 (1964)]. This enzyme deacylated the peptides, but in addition hydrolyzed some of the peptide bonds so that a variety of peptide products resulted.

In 1978 Weber and Perlman reported that a Corynebacterium isolated from soil inactivated the peptide antibiotic amphomycin by deacylation of the isotridecanoic acid side chain [see J. Antibiotics 31 (4), 373-374 (1978)].

Kuwana et al. in U.S. Pat. No. 4,050,989, issued in 1977, described the deacylation of pepsin-inhibiting peptides (pepsidines) by an enzyme from Bacillus pumilus and the use of these products to prepare N-acyl-pentapeptide homologs.

Shoji and coworkers deacylated the cyclic peptide antibiotics cerexin A, cerexin B, and brevistin in order to determine the structures of these antibiotics [see J. Shoji and T. Kato, J. Antibiotics 28, 764-769 (1975) and ibid. 29 (4), 380-389 (1976); and J. Shoji et al., ibid. 29 (12), 1268-1274 (1976); and ibid. 29 (12), 1275-1280 (1976)]. Deacylation was accomplished with an enzyme preparation prepared from Pseudomonas sp. M-6-3 (polymyxin acylase) and by chemical means. Chemical deacylation, however, resulted in extensive side reactions.

Despite the contributions of these groups, it is extremely difficult, when confronted with the problem of deacylating a peptide antibiotic having a different structure, to know whether an enzyme exists which can be used for this purpose. Finding such an enzyme is even more difficult when the substrate antibiotic contains a cyclic peptide nucleus. Enzymes have a high degree of specificity. Differences in the peptide moiety and in the side chain of the substrate antibiotic will affect the outcome of the deacylation attempt. In addition, many microorganisms make a large number of peptidases which attack different portions of the peptide moiety. This frequently leads to intractable mixtures of products.

Thus, it was most surprising that what may be the same enzyme which was used to deacylate penicillins and the A-30912 antibiotics could also be used successfully to deacylate the A-21978C antibiotics. In each of the A-21978C antibiotics (formula 2), the fatty acid side chain ($R^N$) is attached at the α-amino group of the tryptophan residue. In the co-pending application, of Bernard J. Abbott, Manuel Debono and David S. Fukuda entitled "A-21978C CYCLIC PEPTIDES", Ser. No. 380,497 filed May 21, 1982, the full disclosure of which is incorporated herein by reference, is described the discovery that the fatty acid side chain can be cleaved by an enzyme without affecting the chemical integrity of the remainder of the A-21978C peptide.

The enzyme used to effect the deacylation reaction is produced by a microorganism of the family Actinoplanaceae, preferably the microorganism *Actinoplanes utahensis* NRRL 12052, or a variant thereof. To accomplish deacylation, an antibiotic selected from A-21978C complex, A-21978C factors $C_0$, $C_1$, $C_2$, $C_3$, $C_4$, and $C_5$, blocked A-21978C complex, and blocked A-21978C factors $C_0$, $C_1$, $C_2$, $C_3$, $C_4$, and $C_5$ is added to a culture of the microorganism. The culture is allowed to incubate with the substrate until the deacylation is substantially complete. The corresponding A-21978C cyclic peptide thereby obtained is separated from the fermentation broth by methods known in the art.

The cyclic peptides obtained by these enzymatic deacylations are shown in formula 3.

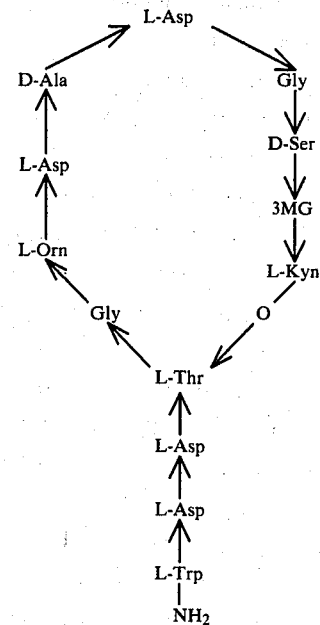

4

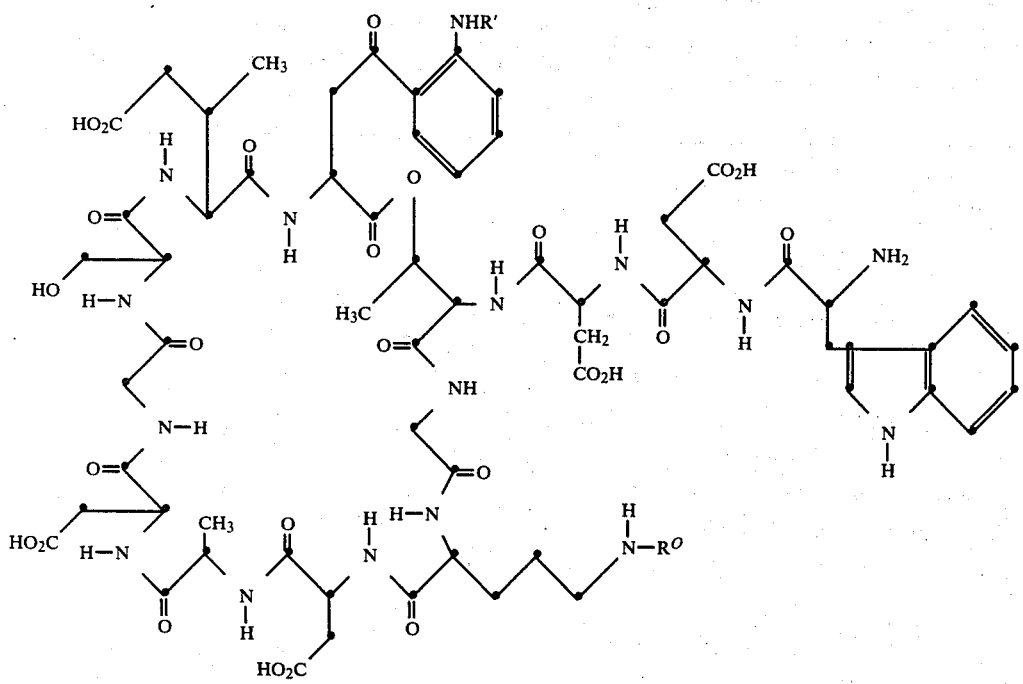

3 wherein R° and R' are, independently, hydrogen or an amino-protecting group; and the salts thereof.

Removal of the acyl moiety from the A-21978C complex or A-21978C individual factors $C_0$, $C_1$, $C_2$, $C_3$, $C_4$, and $C_5$ gives the compound of formula 3 wherein R° and R' each represent hydrogen, which is the common cyclic peptide present in antibiotic A-21978C factors. For convenience herein, this compound will be called A-21978C nucleus. This compound can also be represented by formula 4:

wherein 3MG represents L-threo-3-methylglutamic acid.

The compounds of formula 3 wherein R° or R' are other than hydrogen are prepared by deacylation of appropriately blocked antibiotic A-21978C factors $C_0$, $C_1$, $C_2$, $C_3$, $C_4$ and $C_5$. For convenience herein, these compounds will be called blocked A-21978C nuclei. These blocked compounds are useful intermediates to certain peptides of formula 1, e.g. those compounds wherein $R^1$ is an amino-protecting group.

As will be apparent to those skilled in the art, A-21978C nucleus and blocked A-21978C nuclei can be obtained either in the form of free amines or of acid addition salts. Although any suitable acid addition salt may be used, those which are non-toxic and pharmaceutically acceptable are preferred.

The method of preparing the A-21978C nuclei of formula 3 from the corresponding A-21978C antibiotic by means of fermentation using *Actinoplanes utahensis* NRRL 12052 is described in the co-pending application of Abbott et al., Ser. No. 380,497. *A. utahensis* NRRL 12052 is available to the public from the Agricultural Research Culture Collection (NRRL), Northern Regional Research Center, U.S. Department of Agriculture, 1815 N. University St., Peoria, Ill. 61604, U.S.A., under the accession number NRRL 12052. Preparation 1 herein illustrates the preparation of A-21978C nucleus by fermentation using the A-21978C complex as the substrate and *Actinoplanes utahensis* NRRL 12052 as the microorganism.

Other Actinoplanaceae cultures which can be used to prepare the A-21978C nuclei of formula 3 are available to the public from the Northern Regional Research Laboratory under the following accession numbers:

| | |
|---|---|
| *Actinoplanes missouriensis* | NRRL 12053 |
| Actinoplanes sp. | NRRL 8122 |
| Actinoplanes sp. | NRRL 12065 |
| *Streptosporangium roseum* var. *hollandensis* | NRRL 12064 |

The effectiveness of any given strain of microorganism within the family Actinoplanaceae for carrying out the deacylation is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Micrococcus luteus* assay. Loss of antibiotic activity is an indication that the microorganism produces the requisite enzyme for deacylation. This must be verified, however, using one of the following methods: (1) analysis by HPLC for presence of the intact nucleus; or (2) re-acylation with an appropriate side chain (e.g. lauroyl, n-decanoyl or n-dodecanoyl) to restore activity.

The present invention relates to novel compounds derived by acylating an A-21978C nucleus (compound of formula 3). The compounds of the present invention have the chemical structure depicted in formula 1:

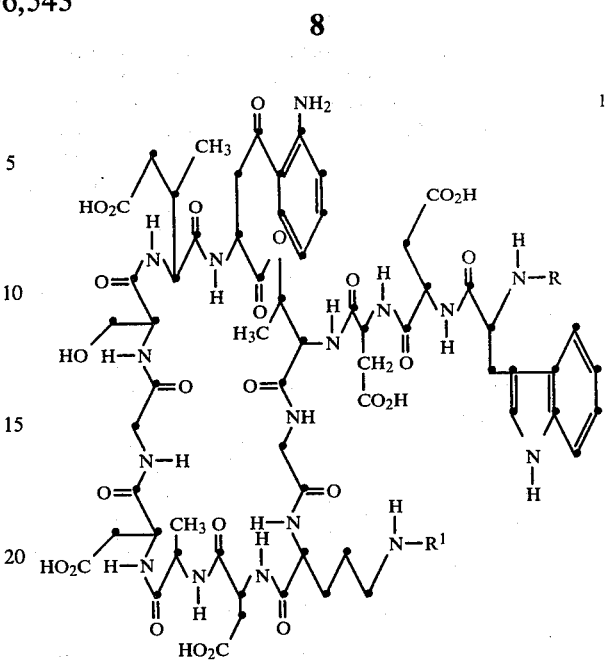

wherein R is hydrogen, 8-methyldecanoyl, 10-methyldodecanoyl, 10-methylundecanoyl, the specific $C_{10}$-alkanoyl group of A-21978$C_0$ or the specific $C_{12}$-alkanoyl groups of A-21978C factors $C_4$ and $C_5$, an amino-protecting group, an aminoacyl group of the formula

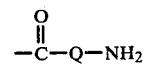

wherein Q is $C_1$-$C_{16}$ alkylene, or an N-alkanoylaminoacyl group of the formula

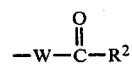

wherein:

W is a divalent aminoacyl radical of the formula:

wherein A is $C_1$-$C_1$ alkylene or $C_5$-$C_6$ cycloalkylene;

wherein $R^3$ is hydroxymethyl, hydroxyethyl, mercaptomethyl, mercaptoethyl, methylthioethyl, 2-thienyl, 3-indole-methyl, phenyl, benzyl, or substituted phenyl or substituted benzyl in which the benzene ring thereof is substituted with chloro, bromo, iodo, nitro, $C_1$-$C_3$ alkyl, hydroxy, $C_1$-$C_3$ alkoxy, $C_1$-$C_3$ alkylthio, carbamyl, or $C_1$-$C_3$ alkylcarbamyl;

(c)
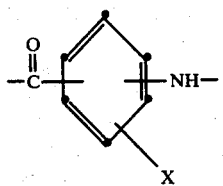

wherein X is hydrogen chloro, bromo, iodo, amino, nitro, $C_1$-$C_3$ alkyl, hydroxy, $C_1$-$C_3$ alkoxy, mercapto, $C_1$-$C_3$ alkylthio, carbamyl, or $C_1$-$C_3$ alkylcarbamyl;

(d)
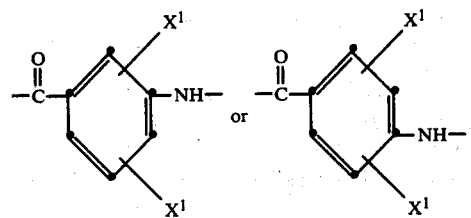

wherein $X^1$ is chloro, bromo, iodo, amino, hydroxy, $C_1$-$C_3$-alkyl or $C_1$-$C_3$-alkoxy;

(e)
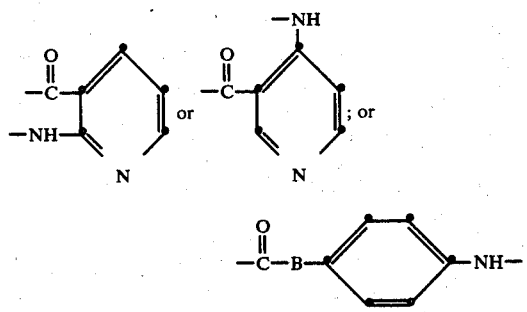

(f)

wherein B is a divalent radical of the formula: $-(CH_2)_n-$ and n is an integer from 1 to 3; $-CH=CH-$; $-CH=CH-CH_2-$; or

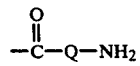

$R^2$ is $C_1$-$C_{17}$ alkyl or $C_2$-$C_{17}$ alkenyl; and
$R^1$ is hydrogen, amino-protecting group, an aminoacyl group of the formula

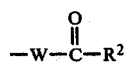

as herein defined, or an N-alkanoylaminoacyl group of the formula $$-W-\overset{O}{\underset{\|}{C}}-R^2$$

as herein defined; provided that, when R is other than aminoacyl or N-alkanoylaminoacyl, $R^1$ must be aminoacyl or N-alkanoylaminoacyl; and, when $R^1$ is an amino-protecting group, R must be aminoacyl or N-alkanoylaminoacyl; and the salts thereof.

As used herein the terms "alkylene", "alkyl", "alkoxy", "alkylthio", and "alkenyl" comprehend both straight and branched hydrocarbon chains. "Alkyl" means a univalent saturated hydrocarbon radical. "Alkenyl" means a univalent unsaturated hydrocarbon radical containing one, two, or three double bonds, which may be oriented in the cis or trans configuration. "Alkylene" means a divalent saturated hydrocarbon radical. "Cycloalkylene" means a divalent cyclic saturated hydrocarbon radical.

Illustrative $C_1$-$C_{10}$ or $C_1$-$C_{16}$ alkylene radicals which are preferred for purposes of this invention are:
$-CH_2-$;

in which $R^5$ is $C_1$-$C_4$ alkyl (i.e., methyl, ethyl, n-propyl, i-propyl, n-butyl, t-butyl, i-butyl, or 1-methylpropyl);
$-(CH_2)_m-$ in which m is an integer from 2 to 10; and

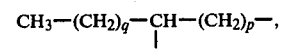

in which p is an integer from 1 to 8 and q is an integer from 0 to 7, provided that p+q must be no greater than 8.

Illustrative $C_1$-$C_{17}$ alkyl groups which are preferred for the purposes of this invention are:
(a) $CH_3-$;
(b) $-(CH_2)_nCH_3$ wherein n is an integer from 1 to 16; and
(c)

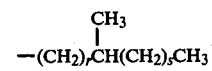

wherein r and s are, independently, an integer from 0 to 14 provided that r+s can be no greater than 14.

Illustrative $C_2$-$C_{17}$ alkenyl radicals, which are preferred for the purpose of this invention, are
(a) $-(CH_2)_t-CH=CH-(CH_2)_u-CH_3$ wherein t and u are, independently, an integer from 0 to 14 provided that t+u can be no greater than 14.
(b) $-(CH_2)_v-CH=CH-(CH_2)_y-CH=CH-(CH_2)_z-CH_3$ wherein v and z are, independently, an integer from 0 to 11 and y is an integer from 1 to 12 provided that v+y+z can be no greater than 11.

In particular, the following embodiments of the $C_1$-$C_{17}$ alkyl groups are preferred:
$CH_3-$
$CH_3(CH_2)_5-$
$CH_3(CH_2)_6-$
$CH_3(CH_2)_8-$
$CH_3(CH_2)_{10}-$
$CH_3(CH_2)_{12}-$
$CH_3(CH_2)_{14}-$
$CH_3(CH_2)_{16}-$ In particular, the following embodiments of the $C_2$-$C_{17}$ alkenyl groups are preferred:
cis—$CH_3(CH_2)_5CH=CH(CH_2)_7-$
trans—$CH_3(CH_2)_5CH=CH(CH_2)_7-$
cis—$CH_3(CH_2)_{10}CH=CH(CH_2)_4-$
trans—$CH_3(CH_2)_{10}CH=CH(CH_2)_4-$
cis—$CH_3(CH_2)_7CH=CH(CH_2)_7-$
trans—$CH_3(CH_2)_7CH=CH(CH_2)_7-$ cis—CH₃(CH₂)₅CH=CH(CH₂)₉—
trans—CH₃(CH₂)₅CH=CH(CH₂)₉—
cis, cis—CH₃(CH₂)₄CH=CHCH₂CH=CH(CH₂)₇—
trans, trans—CH₃(CH₂)₄CH=CHCH₂CH=CH(CH₂)₇—
cis,cis,cis—CH₃CH₂CH=CHCH₂CH=CHCH₂CH=CH—(CH₂)₇—.

When "W" is a divalent radical of the formula

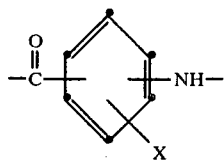

it will be recognized by those skilled in the art that the

function and the —NH—function may be oriented on the benzene ring in the ortho, meta, or para configuration relative to each other. The substituent represented by X may be substituted at any available position of the benzene ring. Preferred embodiments are those in which X is hydrogen and the

and —NH— functions are oriented in the para configuration.

The terms "substituted phenyl" and "substituted benzyl", as defined by R³ in formula 1, contemplate substitution of a group at any of the available positions in the benzene ring—i.e. the substituent may be in the ortho, meta, or para configuration. The term "C₁-C₃ alkyl" as defined by R³ or X in formula 1 includes the methyl, ethyl, n-propyl, or i-propyl groups.

Illustrative R and/or R¹ aminoacyl and N-alkanoylaminoacyl groups are provided in the Examples, infra. Other such illustrative R and/or R¹ groups are:
4-[N-(n-octanoyl)amino]cyclohexan-1-carbonyl,
7-[N-(n-heptanoyl)amino]-n-octanoyl,
α-hydroxymethyl-α-[N-(n-pentadecanoyl)amino]acetyl,
α-(m-methoxyphenyl)-α-[N-(n-heptanoyl)amino]acetyl,
m-chloro-p-[N-(n-nonanoyl)amino]benzoyl,
2,4-dihydroxy-5-[N-(n-decanoyl)amino]benzoyl,
4-[N-(3-methylbutanoyl)amino]nicotinoyl,
4-[N-(n-heptadecanoyl)amino]phenylpropionyl and
p-[N-(n-hexadecanoyl)amino]hippuryl.

The compounds of formula 1 are capable of forming salts. These salts are also part of this invention. Such salts are useful, for example, for separating and purifying the compounds. Pharmaceutically-acceptable alkali-metal, alkaline-earth-metal, amine and acid-addition salts are particularly useful.

For example, the compounds of formula 1 have five free carboxyl groups which can form salts. Partial, mixed and complete salts of these carboxyl groups are, therefore, contemplated as part of this invention. In preparing these salts, pH levels greater than 10 should be avoided due to the instability of the compounds at such levels.

Representative and suitable alkali-metal and alkaline-earth metal salts of the compounds of formula 1 include the sodium, potassium, lithium, cesium, rubidium, barium, calcium and magnesium salts. Suitable amine salts of the formula 1 compounds include the ammonium and the primary, secondary, and tertiary C₁-C₄-alkylammonium and hydroxy-C₂-C₄-alkylammonium salts. Illustrative amine salts include those formed by reaction of a formula 1 compound with ammonium hydroxide, methylamine, sec-butylamine, isopropylamine, diethylamine, di-isopropylamine, cyclohexylamine, ethanolamine, triethylamine, 3-amino-1-propanol and the like.

The alkali-metal and alkaline-earth-metal cationic salts of the compounds of formula 1 are prepared according to procedures commonly used for the preparation of cationic salts. For example, the free acid form of a formula 1 compound is dissolved in a suitable solvent such as warm methanol or ethanol; a solution containing the stoichiometric quantity of the desired inorganic base is aqueous methanol is added to this solution. The salt thus formed can be isolated by routine methods, such as filtration or evaporation of the solvent.

The salts formed with organic amines can be prepared in a similar manner. For example, the gaseous or liquid amine can be added to a solution of a formula 1 compound in a suitable solvent such as ethanol; the solvent and excess amine can be removed by evaporation.

The compounds of this invention also have free amino groups and can, therefore, form acid addition salts. Such salts are also part of this invention. Representative and suitable acid-addition salts of the compounds of formula 1 include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicylic, methanesulfonic, benzenesulfonic, sorbic, picric, benzoic, cinnamic and like acids.

The compounds of formula 1 are prepared by acylating a compound of formula 3 at the α-amino group of tryptophan with the appropriate N-alkanoylaminoacyl or N-alkenoylaminoacyl side chain using methods conventional in the art for forming an amide bond. The acylation is accomplished, in general, by reacting the formula 3 compound with an activated derivative of the acid (formula 5) corresponding to the desired acyl side chain group.

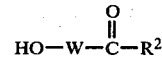    5

(W and R² have the meaning described herein supra). By the term "activated derivative" is meant a derivative which renders the carboxyl function of the acylating agent reactive to coupling with the primary amino group to form the amide bond which links the acyl side chain to the nucleus. Suitable activated derivatives, their methods of preparation, and their methods of use as acylating agents for a primary amine will be recognized by those skilled in the art. Preferred activated derivatives are: (a) an acid halide (e.g. acid chloride), (b) an acid anhydride (e.g. an alkoxyformic acid anhydride or aryloxyformic acid anhydride) or (c) an activated ester (e.g. a 2,4,5-trichlorophenyl ester, an N-hydroxybenztriazole ester, or an N-hydroxysuccinimide ester). Other methods for activating the carboxyl derivatives wherein the $N_{Trp}$-acyl group is that of a natural A-21978C factor are represented by general formula 8.

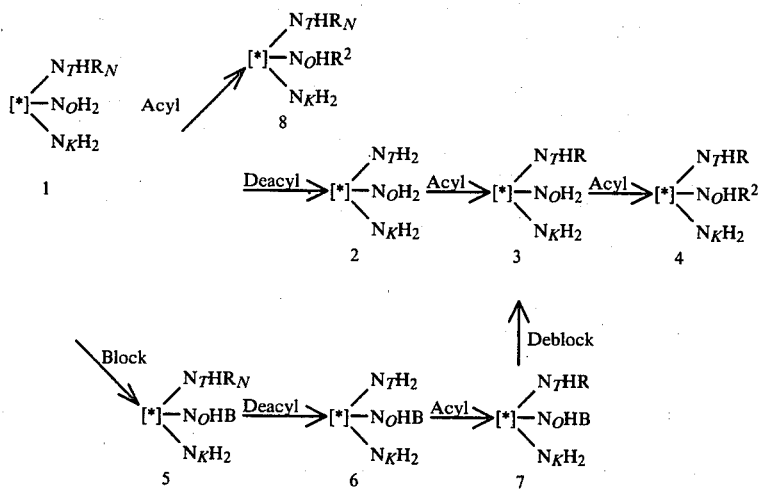

Scheme I: Preparation of $N_{Trp}$—Monoacyl and $N_{Trp}$, $N_{Orn}$—Diacyl-A21978C Derivatives function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

It will be recognized by those skilled in the art that the compounds of formula 1 are prepared using selective acylation procedures and with the assistance of amino-protecting groups. For example, when a compound of formula 3 wherein R° and R' are hydrogen is the starting material, acylation can occur at both the α-amino group of tryptophan and the δ-amino group of ornithine to give $N_{Trp}$, $N_{Orn}$-diacyl derivatives. To obtain derivatives monoacylated at the α-amino group of tryptophan, therefore, it is preferable to acylate a compound of formula 3 wherein the δ-amino group of ornithine (the R° position) is blocked by an amino-protecting group. Such starting materials are preferably obtained by blocking the A-21978C factor at this position before it is deacylated. The aromatic amino group of kynurenine (the R' position) is the least reactive of the three free amino groups in the A-21978C nucleus. Thus, acylation at the R or R¹ position does not usually involve blocking this amino group.

Scheme I outlines general procedures for the preparation of the compounds of formula 1. In this Scheme the following symbols are used:
[*] = remainder of A-21978C
$N_T$ = α-amino group of tryptophan
$N_O$ = δ-amino group of ornithine
$N_K$ = aromatic amino group of kynurenine
R, R¹ = substituents as defined
$R_N$ = acyl group of natural factor
B = amino-protecting group
Acyl = an acylation step
Deacyl = a deacylation step
Block = acylation with an amino-protecting group
Deblock = removal of an amino-protecting group In Scheme I the $N_{Trp}$-monoacyl derivatives of A-21978C are represented by general formula 3 and the $N_{Trp}$, $N_{Orn}$-diacyl derivatives of A-21978C are represented by general formula 4. Those $N_{Trp}$, $N_{Orn}$-diacyl A preferred method for preparing the compounds of formula 1 is by the active ester method, using the compound of formula 3 wherein R'=H and R°=t-BOC, i.e. the A-21978C $N_{Orn}$-t-BOC nucleus or "tBOC nucleus". The use of the 2,4,5-trichlorophenyl ester of the desired N-alkanoylamino acid or N-alkenoylamino acid (formula 5) as the acylating agent is most preferred. In this method, an excess amount of the active ester is reacted with the t-BOC nucleus at room temperature in a non-reactive organic solvent such as DMF, THF, diethyl ether or dichloromethane. The reaction time is not critical, although a time of about 15 to about 18 hours is preferred. At the conclusion of the reaction, the solvent is removed, and the residue is purified. A particularly useful purification method is column chromatography, using silica gel as the stationary phase and ethyl acetate:methanol (3:2, v:v) as the solvent system. The t-BOC group is removed by treatment with trifluoroacetic acid/anisole/triethylsilane or, preferably, trifluoroacetic acid/1,2-ethanedithiol for from about three to about five minutes at room temperature. After the solvent is removed, the residue is purified by reversed-phase HPLC.

The 2,4,5-trichlorophenyl esters of the N-alkanoylamino acids or N-alkenoylamino acids can be prepared conveniently by treating the desired amino acid (formula 5) with 2,4,5-trichlorophenol in the presence of a coupling agent, such as N,N'-dicyclohexylcarbodiimide. Other methods suitable for preparing amino acid esters will be apparent to those skilled in the art.

The N-alkanoylamino acids or N-alkenoylamino acids are either known compounds or they can be made by acylating the appropriate amino acid with the desired alkanoyl or alkenoyl group using conventional methods, such as those described herein supra. A preferred way of preparing the N-alkanoylamino acids is by treating the appropriate amino acid with an alkanoic acid chloride in pyridine. The alkanoic acids or alkenoic acids, the activated derivatives thereof, and the amino acids used in the preparation of the products of this invention are either known compounds or they can be made by known methods or by modification of known methods which will be apparent to those skilled in the art.

If a particular amino acid contains an acylable functional group other than the amino group, it will be understood by those skilled in the art that such a group must be protected prior to reaction of the amino acid with the reagent used to attach the alkanoyl or alkenoyl group. Suitable protecting groups can be any group known in the art to be useful for the protection of a side chain functional group in peptide synthesis. Such groups are well known, and the selection of a particular protecting group and its method of use will be readily known to one skilled in the art [see, for example, "Protective Groups In Organic Chemistry", M. McOmie, Editor, Plenum Press, N.Y., 1973].

It will be recognized that certain amino acids used in the synthesis of the products of this invention may exist in optically active forms, and both the natural configuration (L-configuration) and unnatural configuration (D-configuration) may be used as starting materials and will give products which are within the contemplation of this invention.

When an A-21978C cyclic peptide of this invention is used as an antibacterial agent, it may be administered either orally or parenterally. As will be appreciated by those skilled in the art, the A-21978C compound is commonly administered together with a pharmaceutically acceptable carrier or diluent. The dosage of A-21978C compound will depend upon a variety of considerations, such as, for example, the nature and severity of the particular infection to be treated. Those skilled in the art will recognize that appropriate dosage ranges and/or dosage units for administration may be determined by considering the MIC and ED$_{50}$ values and toxicity data herein provided together with factors such as pharmacokinetics, the patient or host and the infecting microorganism.

The methods of making and using the compounds of the present invention are illustrated in the following examples:

PREPARATION 1

Preparation of A-21978C Nucleus

A. Fermentation of *Actinoplanes utahensis*

A stock culture of *Actinoplanes utahensis* NRRL 12052 is prepared and maintained on an agar slant. The medium used to prepare the slant is selected from one of the following:

| MEDIUM A | |
|---|---|
| Ingredient | Amount |
| Pre-cooked oatmeal | 60.0 g |
| Yeast | 2.5 g |
| K$_2$HPO$_4$ | 1.0 g |
| Czapek's mineral stock* | 5.0 ml |
| Agar | 25.0 g |
| Deionized water | q.s. to 1 liter | pH before autoclaving is about 5.9; adjust to pH 7.2 by addition of NaOH; after autoclaving, pH is about 6.7.
*Czapek's mineral stock has the following composition:

| Ingredient | Amount |
|---|---|
| FeSO$_4$.7H$_2$O (dissolved in 2 ml conc HCl) | 2 g |
| KCl | 100 g |
| MgSO$_4$.7H$_2$O | 100 g |
| Deionized water | q.s. to 1 liter |

| MEDIUM B | |
|---|---|
| Ingredient | Amount |
| Potato dextrin | 5.0 g |
| Yeast extract | 0.5 g |
| Enzymatic hydrolysate of casein* | 3.0 g |
| Beef extract | 0.5 g |
| Glucose | 12.5 g |
| Corn starch | 5.0 g |
| Meat peptone | 5.0 g |
| Blackstrap molasses | 2.5 g |
| MgSO$_4$.7H$_2$O | 0.25 g |
| CaCO$_3$ | 1.0 g |
| Czapek's mineral stock | 2.0 ml |
| Agar | 20.0 g |
| Deionized water | q.s. to 1 liter |

*N—Z-Amine A, Humko Sheffield Chemical, Lyndhurst, NJ.

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
|---|---|
| Pre-cooked oatmeal | 20.0 g |
| Sucrose | 20.0 g |
| Yeast | 2.5 g |
| Distiller's Dried Grain* | 5.0 g |
| K$_2$HPO$_4$ | 1.0 g |
| Czapek's mineral stock | 5.0 ml |
| Deionized water | q.s. to 1 liter | adjust to pH 7.4 with NaOH; after autoclaving, pH is about 6.8.
*National Distillers Products Co., 99 Park Ave., New York, NY.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen", *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (80 ml), prepared as above-described, is used to inoculate 10 liters of sterile production medium selected from one of the following:

| MEDIUM I | |
|---|---|
| Ingredient | Amount (g/L) |
| Peanut meal | 10.0 |
| Soluble meat peptone | 5.0 |
| Sucrose | 20.0 |
| KH$_2$PO$_4$ | 0.5 |
| K$_2$HPO$_4$ | 1.2 |
| MgSO$_4$.7H$_2$O | 0.25 |
| Tap water | q.s. to 1 liter |

The pH of the medium is about 6.9 after sterilization by autoclaving at 121° C. for 45 minutes at about 16–18 psi.

| MEDIUM II | |
|---|---|
| Ingredient | Amount (g/L) |
| Sucrose | 30.0 |
| Peptone | 5.0 |
| K$_2$HPO$_4$ | 1.0 |
| KCl | 0.5 |
| MgSO$_4$.7H$_2$O | 0.5 |
| FeSO$_4$.7H$_2$O | 0.002 |
| Deionized water | q.s. to 1 liter |

Adjust to pH 7.0 with HCl; after autoclaving, pH is about 7.0.

| MEDIUM III | |
|---|---|
| Ingredient | Amount (g/L) |
| Glucose | 20.0 |
| NH$_4$Cl | 3.0 |
| Na$_2$SO$_4$ | 2.0 |
| ZnCl$_2$ | 0.019 |
| MgCl$_2$.6H$_2$O | 0.304 |
| FeCl$_3$.6H$_2$O | 0.062 |
| MnCl$_2$.4H$_2$O | 0.035 |
| CuCl$_2$.2H$_2$O | 0.005 |
| CaCO$_3$ | 6.0 |
| KH$_2$PO$_4$* | 0.67 |
| Tap water | q.s. to 1 liter |

*Sterilized separately and added aseptically
Final pH about 6.6.

The inoculated production medium is allowed to ferment in a 14-liter fermentation vessel at a temperature of about 30° C. for about 66 hours. The fermentation medium is stirred with conventional agitators at about 600 RPM and aerated with sterile air to maintain the dissolved oxygen level above 30% of air saturation at atmospheric pressure.

B. Deacylation of A-21978C

A fermentation of *A. utahensis* is carried out as described in Section A, using slant medium A and production medium I and incubating the production medium for about 67 hours. Crude A-21978C complex (100 g), prepared as described in U.S. Pat. No. 4,208,403, is added to the fermentation medium.

Deacylation of the A-21978C complex is monitored by assay against *Micrococcus luteus*. The fermentation is allowed to continue until deacylation is complete as indicated by disappearance of activity vs. *M. luteus*, a period of about 24 hours.

C. Isolation of A-21978C Nucleus

Whole fermentation broth (20 liters), obtained as described in Section B, was filtered with a filter aid (Hyflo Super-Cel, Johns Manville Corp.). The mycelial cake was discarded. The filtrate thus obtained was passed through a column containing 1.5 liters of HP-20 resin (DIAION High Porous Polymer, HP-Series, Mitsubishi Chemical Industries Limited, Tokyo, Japan). The effluent thus obtained was discarded. The column was then washed with deionized water (10 L.) to remove residual filtered broth. This wash water was discarded. The column was then eluted with water-:acetonitrile mixtures (10 L. each of 95:5, 9:1, and 4:1), collecting 1-liter fractions.

Elution was monitored by analytical HPLC, using silica gel/C$_{18}$ and a solvent system of water: methanol (3:1) containing 0.1% ammonium acetate, detecting the nucleus with a UV monitor at 254 nm. Fractions containing the nucleus were combined, concentrated under vacuum to remove the acetonitrile and freeze-dried to give 40.6 g of semi-purified A-21978C nucleus.

D. Purification of A-21978C Nucleus

Semi-purified A-21978C nucleus (15 g), obtained as described in Section C, was dissolved in 75 ml of water:-methanol:acetonitrile (82:10:8) containing 0.2% acetic acid and 0.8% pyridine. This solution was pumped onto a 4.7-×192-cm column containing 3.33 L. of silica gel (Quantum LP-1)/C$_{18}$. The column was developed with the same solvent system. Fractions having a volume of 350 ml were collected. Separation was monitored at 280 nm with a UV monitor. Fractions containing the nucleus were combined, concentrated under vacuum to remove solvents and freeze-dried to give 5.2 g of purified A-21978C nucleus.

E. Characteristics of A-21978C Nucleus

A-21978C nucleus has the following characteristics:

(a) Form: white amorphous solid which fluoresces under short-wave UV (b) Empirical formula: $C_{62}H_{82}N_{16}O_{26}$ (c) Molecular weight: 1466

(d) Solubility: soluble in water (e) Infrared absorption spectrum (KBr disc) shows absorption maxima at the following frequencies (cm$^{-1}$): 3300 (broad), 3042 (weak), 2909 (weak), 1655 (strong), 1530 (strong), 1451 (weak), 1399 (medium), 1222 (medium), 1165 (weak), 1063 (weak) and 758 (medium to weak)

(f) UV absorption spectrum in methanol shows maxima at 223 nm ($\epsilon$ 41,482) and 260 nm ($\epsilon$ 8,687)

(g) Electrometric titration in 66% aqueous dimethylformamide indicates the presence of four titratable groups with pK$_a$ values of about 5.2, 6.7, 8.5 and 11.1 (initial pH 6.12).

PREPARATION 2

Alternate Preparation of A-21978C Nucleus

A-21978C nucleus was prepared according to the method of Preparation 1 except for certain changes in Section B. The *A. utahensis* culture was incubated initially for about 48 hours; the substrate was semipurified A21978C complex (50 g); and incubation after addition of the substrate was about 16 hours. The broth filtrate was passed over a column containing 3.1 liters of HP-20 resin. The column was washed with 10 volumes of water and then was eluted with water:acetonitrile (95:5). Elution was monitored as in Preparation 1. After collecting 24 liters, the eluting solvent was changed to water:acetonitrile (9:1). Fractions containing the nucleus were eluted with this solvent. These fractions were combined, concentrated under vacuum to remove acetonitrile, and freeze-dried to give 24.3 g of semi-purified A-21978C nucleus.

This semi-purified A-21978C nucleus (24.3 g) was dissolved in water (400 ml). The solution was pumped onto a 4.7-×192-cm steel column containing 3.33 liters of silica gel (Quantum LP-1)/$C_{18}$ prepared in water:methanol:acetonitrile (8:1:1) containing 0.2% acetic acid and 0.8% pyridine. The column was developed with the same solvent at a pressure of about 2000 psi, collecting 350 ml fractions. Elution was monitored by UV at 280 nm. Fractions containing the nucleus were combined, concentrated under vacuum to remove solvents, and freeze-dried to give 14 g of highly purified A-21978C nucleus.

PREPARATION 3

Preparation of $N_{Orn}$-t-BOC-A-21978C Factors $C_2$ and $C_3$

A mixture of A-21978C factors $C_2$ and $C_3$ (10 g), prepared as described in U.S. Pat. No. 4,208,403, was dissolved in water (50 ml) with sonication (200 mg/ml). The pH of the solution was adjusted from 4.05 to 9.5 with 5 N NaOH (3.6 ml). Di-tert-butyl dicarbonate (3.0 ml) was added, and the reaction mixture was stirred at room temperature for 2 hours. The pH of the reaction was maintained at 9.5 by manual addition of 5 N NaOH (6.5 ml added in 2 hours).

The reaction was monitored periodically by TLC on silica gel, using $CH_3CN:H_2O$ (7:3 and 8:2) solvent systems and detecting by UV.

After about 10 minutes and reaction solution became rapidly turbid, and base consumption increased. After 30 minutes, the rate of increase in turbidity and the rate of base consumption decreased, indicating that the reaction was complete. Nevertheless, the reaction was continued for an additional 90 minutes to insure completion. At the end of the two-hour reaction, the reaction material was lyophilized immediately to give 12.7 g of $N_{Orn}$-t-BOC-A-21978 factors $C_2$ and $C_3$.

Using similar procedures, two 10-g reactions and a 30-g reaction were run. In each of these the reaction time was only 40 minutes. The two 10-g experiments gave 11.9 and 12.1 g of product, respectively. The 30-g reaction gave 35.4 g of product.

PREPARATION 4

Preparation of A-21978C $N_{Orn}$-t-BOC Nucleus

A. Fermentation of *A. utahensis*

A fermentation of *A. utahensis* was carried out as described in Preparation 1, Section A, using slant medium A and production medium I and incubating the production medium for about 66 hours.

B. Deacylation of $N_{Orn}$-t-BOC Complex

The A-21978C $N_{Orn-t-BOC\ complex}$ (1185 g of crude substrate which contained about 176 g of A-21978C complex) was added to the fermentation medium. Deacylation was carried out as described in Preparation 1, Section B. Deacylation was complete, as indicated by HPLC, after about 24 hours.

C. Isolation of A-21978C $N_{Orn}$-t-BOC Nucleus

Fermentation broth (100 L.), obtained as described in Section B, was filtered with a filter aid (Hyflo Super-cel). The filtrate was passed over a column containing 7.5 L. of HP-20 resin (DIAION); the column was washed with water (38 L.). Elution was monitored by silica gel/$C_{18}$ HPLC with UV detection at 254 nm. Some nucleus was eluted in the wash. Subsequent elution of nucleus was carried out with water:acetonitrile mixtures as follows: (95:5)–40 L.; (9:1)—40 L.; and (85:15)—100 L. Fractions containing the nucleus were combined, concentrated under vacuum to remove solvent, and freeze-dried to give 298.5 g of semi-purified A-21978C $N_{Orn}$-t-BOC nucleus.

D. Purification of A-21978C $N_{Orn}$-t-BOC Nucleus

Semi-purified A-21978C $N_{Orn}$-t-BOC nucleus (30 g), obtained as described in Section C, was dissolved in water:acetonitrile (9:1) containing 0.2% acetic acid and 0.8% pyridine (75 ml). This solution was applied to a 4.7×192-cm steel column containing 3.33 L. of silica gel (Quantum LP-1)/$C_{18}$ equilibrated in the same solvent system. The column was developed under pressure with water:acetonitrile:methanol (80:15:5) containing 0.2% acetic acid and 0.8% pyridine, collecting 350-ml fractions and detecting product by UV at 280 nm. Fractions containing the product were combined, concentrated under vacuum to remove solvent and freeze-dried to give 18.4 g of purified A-21978C $N_{Orn}$-t-BOC nucleus.

A-21978C t-BOC nucleus has the following characteristics:

(a) Form: white amorphous solid which fluoresces under short-wave UV (b) Empirical formula: $C_{67}H_{90}N_{16}O_{28}$ (c) Molecular weight: 1566

(d) Solubility: soluble in water (e) Infrared absorption spectrum (KBr disc) shows absorption maxima at the following frequencies ($cm^{-1}$): 3345 (broad), 3065 (weak), 2975 (weak), 2936 (weak), ~1710 (shoulder), 1660 (strong), 1530 (strong), 1452 (weak), 1395 (medium, 1368 (weak), 1341 (weak), 1250 (medium), 1228 (medium), 1166 (medium to weak) and 1063 (weak)

(f) UV absorption spectrum in 90% ethanol shows maxima at: 220 nm ($\epsilon$42,000) and 260 nm ($\epsilon$10,600).

(g) HPLC retention time=6 min on 4.6-×300-mm silica-gel $C_{18}$ column, using $H_2O/CH_3CN/CH_3OH$ (80:15:5) solvent containing 0.2% $NH_4OAc$ at a flow rate of 2 ml/min with UV detection.

PREPARATION 5

Alternative Purification of A-21978C $N_{Orn}$-t-BOC Nucleus

Semi-purified A-21978C $N_{Orn}$-t-BOC nucleus (10.8 g), obtained as described in Preparation 4, Section C, was dissolved in water and applied to a column containing 80 ml of Amberlite IRA-68 (acetate cycle). The column was washed with water and, at a flow rate of 5 ml/min, was eluted sequentially with 0.05 N acetic acid (1080 ml), 0.1 N acetic acid (840 ml), and 0.2 N acetic acid (3120 ml), collecting 120-ml fractions. The column was monitored with analytical HPLC over silica gel/$C_{18}$, using a system of water:acetonitrile:methanol (80:15:5) containing 0.2% ammonium acetate and detecting product with UV at 254 nm. Fractions containing the product were combined; the pH of the solution was adjusted to 5.8 with pyridine; the resulting solution was concentrated under vacuum to a volume of about 200 ml. Water was added to the concentrate, and the resulting solution was reconcentrated to remove pyridine. This concentrate was freeze-dried to give 3.46 g of purified A-21978C $N_{Orn}$-t-BOC nucleus.

PREPARATIONS 6–14

The preparation of a number of useful N-alkanoylamino acids is described in U.S. Pat. No. 4,293,483 (see Table 1, columns 9–16). Such compounds are prepared according to the following general procedure:

The appropriate alkanoic acid chloride is added dropwise to the appropriate amino acid (1:1 mole ratio) dissolved in pyridine. The amount of pyridine used should be sufficient to make the concentration of reactants between 0.1 to 0.2 M. The solution is stirred at room temperature for about 3 to 6 hours, after which it is poured into a large volume of water. The product precipitates from solution and is collected by filtration and crystallized from methanol.

Other N-alkanoylamino acids prepared by this procedure are summarized in Table 1.

PREPARATIONS 15–24

The 2,4,5-trichlorophenyl esters of the N-alkanoylamino acids described in U.S. Pat. No. 4,293,483 are also described in that patent (see Table 2, columns 17–20). Such compounds are prepared according to the following general procedure:

The N-alkanoylamino acid (1 mole), 2,4,5-trichlorophenol (1.1 mole), and DCC (1 mole) are dissolved in dichloromethane, diethyl ether or THF. The solution is stirred at room temperature for about 16 to about 20 hours after which it is filtered. The filtrate is taken to dryness, and the product is crystallized from either acetonitrile-water or diethyl ether-petroleum ether.

The preparation of other 2,4,5-trichlorophenyl esters of N-alkanoylamino acids prepared by this method is summarized in Table II.

TABLE I
Preparation of N—Alkanoyl Amino Acids

| Prep. No. | Alkanoic acid chloride Formula | wt. (g) | Amino Acid Formula | wt. (g) | N—Alkanoyl Amino Acid Formula | wt. (g) |
|---|---|---|---|---|---|---|
| 6 | $CH_3(CH_2)_6COCl$ | 3.25 | L-phenylalanine | 3.30 | $CH_3(CH_2)_6CONHCH(CH_2C_6H_5)COOH$ | 4.85 |
| 7 | $CH_3(CH_2)_7COCl$ | 2.0 | " | 1.82 | $CH_3(CH_2)_7CONHCH(CH_2C_6H_5)COOH$ | 2.8 |
| 8 | $CH_3(CH_2)_8COCl$ | 3.9 | " | 3.30 | $CH_3(CH_2)_8CONHCH(CH_2C_6H_5)COOH$ | 5.35 |
| 9 | $CH_3(CH_2)_9COCl$ | 4.0 | " | 3.23 | $CH_3(CH_2)_9CONHCH(CH_2C_6H_5)COOH$ | 4.5 |
| 10 | $CH_3(CH_2)_{10}COCl$ | 6.54 | " | 4.95 | $CH_3(CH_2)_{10}CONHCH(CH_2C_6H_5)COOH$ | 5.2 |
| 11 | $CH_3(CH_2)_{11}COCl$ | 2.0 | " | 1.42 | $CH_3(CH_2)_{11}CONHCH(CH_2C_6H_5)COOH$ | 1.7 |
| 12 | $CH_3(CH_2)_{12}COCl$ | 4.8 | " | 3.30 | $CH_3(CH_2)_{12}CONHCH(CH_2C_6H_5)COOH$ | 6.6 |
| 13 | $CH_3(CH_2)_4COCl$ | 6.2 | L-tryptophan | 10.2 | $CH_3(CH_2)_4CONHCH(CH_2\text{-indolyl})COOH$ | 6.82 |
| 14 | $CH_3(CH_2)_{10}COCl$ | 10.9 | " | 10.2 | $CH_3(CH_2)_{10}CONHCH(CH_2\text{-indolyl})COOH$ | 13.8 |

TABLE II
Preparation of 2,4,5-Trichlorophenyl Esters

| Preparation No. | N—Alkanoyl Amino Acid Formula | wt (g) | 2,4,5-Trichlorophenyl Ester Product wt (g) |
|---|---|---|---|
| 15 | $CH_3(CH_2)_6CONHCH(CH_2C_6H_5)COOH$ | 2.9 | 4.1 |
| 16 | $CH_3(CH_2)_7CONHCH(CH_2C_6H_5)COOH$ | 2.8 | 3.86 |
| 17 | $CH_3(CH_2)_8CONHCH(CH_2C_6H_5)COOH$ | 3.19 | 1.5 |
| 18 | $CH_3(CH_2)_9CONHCH(CH_2C_6H_5)COOH$ | 3.29 | 5.01 |
| 19 | $CH_3(CH_2)_{11}CONHCH(CH_2C_6H_5)COOH$ | 1.7 | 2.01 |
| 20 | $CH_3(CH_2)_{12}CONHCH(CH_2C_6H_5)COOH$ | 3.75 | 4.18 |
| 21 | $CH_3(CH_2)_{10}CONH\text{-C}_6H_3(COOH)(OH)$ | 2.1 | 1.6 |
| 22 | $CH_3(CH_2)_{10}CONHCH(CH_2C_6H_5)COOH$ | 3.47 | 3.98 |

TABLE II-continued

Preparation of 2,4,5-Trichlorophenyl Esters

| Preparation No. | N—Alkanoyl Amino Acid Formula | wt (g) | 2,4,5-Trichlorophenyl Ester Product wt (g) |
|---|---|---|---|
| 23 | $CH_3(CH_2)_4CONHCH(COOH)—CH_2$—[indol-3-yl] | 6.04 | 1.87 |
| 24 | $CH_3(CH_2)_{10}CONHCH(COOH)—CH_2$—[indol-3-yl] | 7.76 | 4.03 |

EXAMPLES 1–33

The N-alkanoylamino acid derivatives of A-21978C of formula 1 are prepared according to the following general procedure which involves acylating the nucleus using the activated-ester method:

A solution of $N_{Orn}$-t-BOC-blocked-A-21978C nucleus (t-BOC nucleus) in DMF was treated with the 2,4,5-trichlorophenyl ester ("active ester") of the corresponding N-alkanoylamino acid. The reaction mixture was stirred at room temperature for about 18 to about 24 hours under an atmosphere of nitrogen and then was evaporated to dryness under reduced pressure to give a residue. A small amount of methanol was added to the residue; a solid (N,N'-dicyclohexylurea) which did not dissolve in the methanol was removed by filtration and discarded. The filtrate was evaporated under vacuum to give a solid, the crude $N_{Orn}$-t-BOC-$N_{Trp}$-acyl-A-21978C analog. This analog was purified using a "Prep LC/System 500" unit (Waters Associates, Inc., Milford, Mass.) equipped with a Prep Pak-500/$C_{18}$ column (Waters Associates Inc.) as a stationary phase. The column was eluted isocratically, using a water:methanol:acetonitrile (2:1:2) solvent system containing 0.1% pyridinium acetate, and eluting one 250-ml fraction per minute for approximately 40 fractions. Amounts of sample applied varied from about 1 g to about 5 g. Early fractions containing unreacted starting materials were discarded. The desired product was always the major peak (using a UV detector) following the early fractions. Individual fractions were pooled on the basis of TLC [reversed-phase silica gel ($C_{18}$), a water:methanol:acetonitrile (3:3:4) solvent system, and Von Urk spray for detection] and bioautographic analysis [silica-gel TLC plates (Merck), an acetonitrile:acetone:water (2:2:1) solvent system and *Micrococcus luteus* as the assay organism].

The $N_{Orn}$-t-BOC-$N_{Trp}$-acyl-A-21978C analog, obtained as a single component by this method, was lyophilized and treated with anhydrous trifluoroacetic-acid (10 ml per 0.3–0.5 g of analog) containing 2% anisole at 0° C. After about five minutes the reaction mixture was evaporated to dryness under reduced pressure. The residue obtained was triturated with a small amount of ether. The solid precipitate was collected and air-dried. This material was dissolved in water; the pH of the solution was raised to about 6 to 7 by the addition of pyridine; and the solution was then lyophilized. The resulting product was obtained as a single component and was characterized by its chromatographic properties and its amino-acid analysis.

Table III summarizes a group of $N_{Trp}$-alkanoylaminoacyl A-21978C derivatives prepared by this procedure.

TABLE III

N_Trp—Alkanoylamino Acid Derivatives of A-21978C Cyclic Peptides

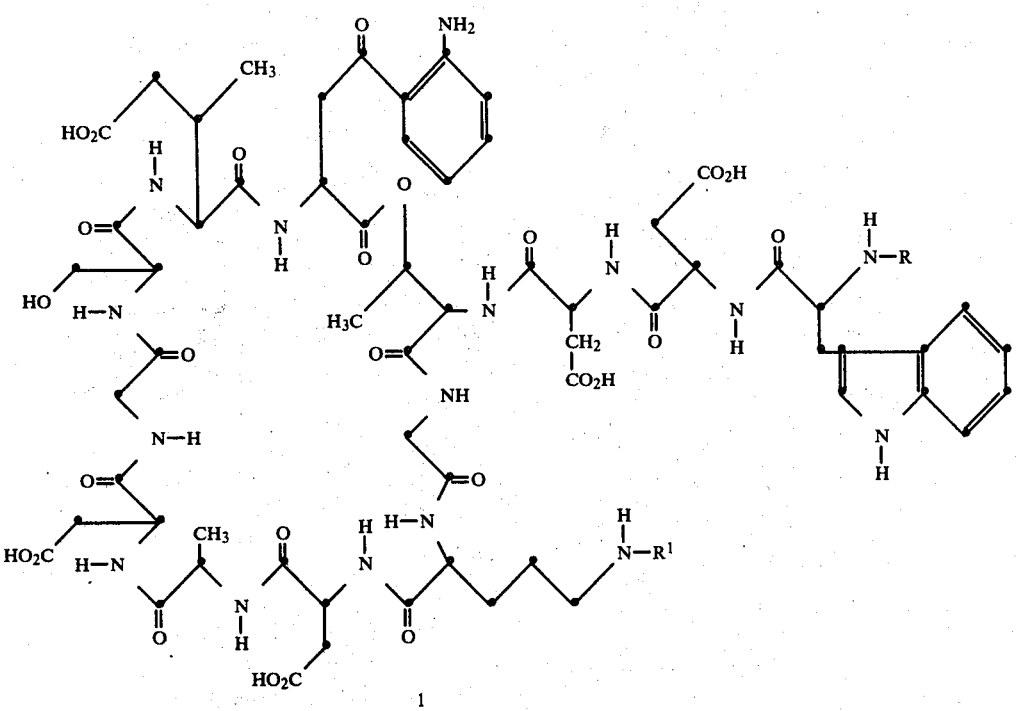

| Example No. | Product[a] R in formula 1 | Ester (mg) | A-21978C Nucleus (mg) | t-BOC A-21978C Product (mg)[b] | Product (mg) | R_f[c] |
|---|---|---|---|---|---|---|
| 1 | (D)CH₃(CH₂)₁₀CONHCH(CH₂C₆H₅)CO— | 900 | 900[d] | 556 | 436 | 0.82 |
| 2 | CH₃(CH₂)₁₀CONH(CH₂)₄—CO— | 900 | 900[d] | 489 | 485 | 0.65 |
| 3 | CH₃(CH₂)₁₀CONH(CH₂)₁₀—CO— | 600 | 900[d] | 326 | 242 | 0.83 |
| 4 | CH₃(CH₂)₁₀CONH—⟨C₆H₄⟩—CO— | 416 | 1000[e] | — | 195 | 0.34 |
| 5 | CH₃(CH₂)₁₀CONH—⟨C₆H₄⟩—CO— | 900 | 900[d] | 352 | 263 | 0.57 |
| 6 | CH₃(CH₂)₁₀CONH—⟨C₆H₃(OH)⟩—CO— | 800 | 800[d] | 76 | 24 | 0.23 |
| 7 | CH₃(CH₂)₁₀CONH—⟨C₆H₂Cl₂⟩—CO— | 800 | 800[d] | 389 | 312 | 0.17 |
| 8 | (L)CH₃(CH₂)₁₀CONHCH(CH₂C₆H₅)CO— | 800 | 800[d] | 421 | 324 | 0.82 |

TABLE III-continued

N_Trp—Alkanoylamino Acid Derivatives of A-21978C Cyclic Peptides

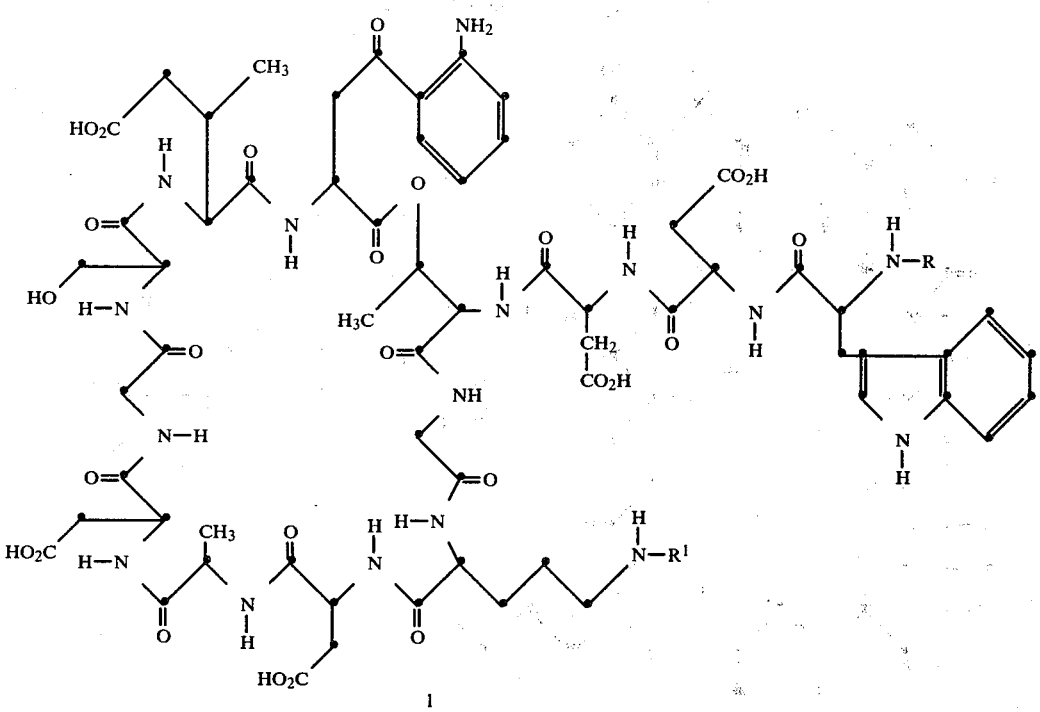

1

| Example No. | Product[a] R in formula 1 | Ester (mg) | A-21978C Nucleus (mg) | t-BOC A-21978C Product (mg)[b] | Product (mg) | $R_f$[c] |
|---|---|---|---|---|---|---|
| 9 | (L)CH₃(CH₂)₄CONHCHCO— [indolylmethyl substituent] | 1000 | 1000 | — | 230 | 0.68 |
| 10 | CH₃(CH₂)₁₀CONH—⟨phenyl⟩—CH₂CO— | 900 | 900[d] | 633 | 485 | 0.74 |
| 11 | trans-CH₃(CH₂)₁₀CONH—⟨phenyl⟩—CH=CH—CO— | 800 | 800[d] | 245 | 186 | 0.58 |
| 12 | CH₃(CH₂)₁₀CONH—⟨phenyl⟩—CONHCH₂—CO— | 350 | 700[d] | 376 | 304 | 0.38 |
| 13 | CH₃(CH₂)₁₀CONH—⟨pyridyl⟩—CO— | 900 | 900[d] | 320 | 218 | 0.65 |
| 14 | CH₃(CH₂)₅CONH(CH₂)₁₀—CO— | 900 | 900[d] | 503 | 428 | 0.60 |
| 15 | CH₃(CH₂)₁₂CONH—⟨phenyl⟩—CO— | 900 | 900[d] | 273 | 212 | 0.83 |

TABLE III-continued
$N_{Trp}$—Alkanoylamino Acid Derivatives of A-21978C Cyclic Peptides

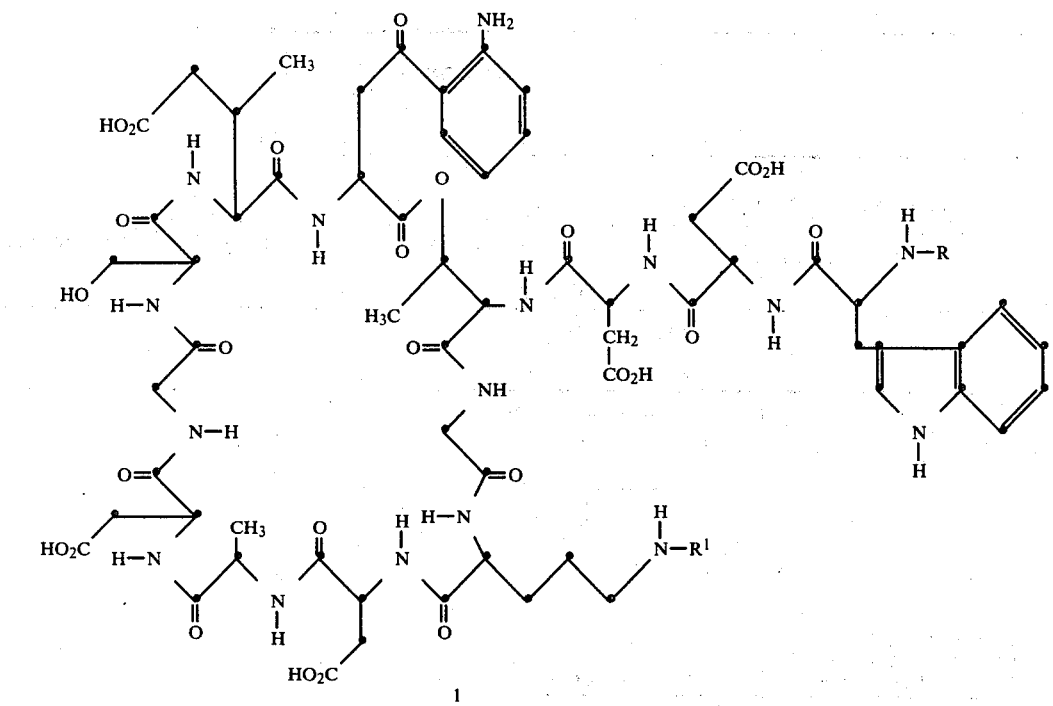

1

| Example No. | Product[a] R in formula 1 | Ester (mg) | A-21978C Nucleus (mg) | t-BOC A-21978C Product (mg)[b] | Product (mg) | $R_f$[c] |
|---|---|---|---|---|---|---|
| 16 | (L)-CH$_3$(CH$_2$)$_{10}$CONH—CH—CO— (with indole CH$_2$ substituent) | 1000 | 1000[d] | 426 | 286 | 0.73 |
| 17 | (L)CH$_3$(CH$_2$)$_6$CONHCH(CH$_2$C$_6$H$_5$)CO— | 800 | 800[d] | 444 | 343 | 0.48 |
| 18 | (L)CH$_3$(CH$_2$)$_7$CONHCH(CH$_2$C$_6$H$_5$)CO— | 800 | 800[d] | 412 | 312 | 0.50 |
| 19 | (L)CH$_3$(CH$_2$)$_8$CONHCH(CH$_2$C$_6$H$_5$)CO— | 800 | 800[d] | 519 | 453 | 0.52 |
| 20 | (L)CH$_3$(CH$_2$)$_9$CONHCH(CH$_2$C$_6$H$_5$)CO— | 800 | 800[d] | 371 | 287 | 0.53 |
| 21 | (L)CH$_3$(CH$_2$)$_{11}$CONHCH(CH$_2$C$_6$H$_5$)CO— | 800 | 800[d] | 412 | 335 | |
| 22 | (L)CH$_3$(CH$_2$)$_{12}$CONHCH(CH$_2$C$_6$H$_5$)CO— | 800 | 800[d] | 468 | 328 | |

[a] $R^1$ = H,
[b] $N_{Orn}$—t-BOC-$N_{Trp}$—Acyl-Nucleus,
[c] Thin-layer chromatography on silica gel (Merck), using a water:CH$_3$CN:acetone (1:2:2) solvent system
[d] $N_{Orn}$—t-BOC—Nucleus,
[e] A21978C Nucleus.

Other N-alkanoylamino acid derivatives of formula 1 prepared in a similar manner are summarized in Table IV.

TABLE IV
A-21978C Cyclic Peptides of Formula 1

| Example No. | R | $R^1$ |
|---|---|---|
| 23 | cis-CH$_3$(CH$_2$)$_{10}$CONH—⟨C$_6$H$_4$⟩—HC=CH—CO— | H |
| 24 | CH$_3$(CH$_2$)$_{10}$CONH—⟨C$_6$H$_4$⟩—CONHCH$_2$CO— | H |

TABLE IV-continued

A-21978C Cyclic Peptides of Formula 1

| Example No. | R | R$^1$ |
|---|---|---|
| 25 | H | $CH_3(CH_2)_{10}CONH$—⟨phenyl⟩—CO— |
| 26 | H | $CH_3(CH_2)_9CONHCH(CH_2C_6H_5)CO$— |

Table V summarizes a group of A-21978C derivatives prepared according to the general procedure, but using A-21978C factors as starting materials.

TABLE V

Diacyl Derivatives of A-21978C

| Example No. | R in formula 1 | R$^1$ in formula 1 | Starting Factor | Ester (mg) | A-21978C Factor (mg) | Product (mg) | R$_f{}^a$ |
|---|---|---|---|---|---|---|---|
| 27 | $CH_3CH_2CH(CH_3)(CH_2)_6CO$— | (L)-$CH_3(CH_2)_4CONHCH$—CO— (indolylmethyl) | $C_1$ | 100 | 48 | 43 | 0.81 |
| 28 | $CH_3CH(CH_3)(CH_2)_8CO$— | " | $C_2$ | 100 | 48 | 25 | 0.73 |
| 29 | $CH_3CH_2CH(CH_3)(CH_2)_8CO$— | " | $C_3$ | 400 | 1000 | 413 | 0.87 |
| 30 | $CH_3CH_2CH(CH_3)(CH_2)_6CO$— | $H_2N(CH_2)_{10}$—CO— | $C_1$ | 1000 | 1000 | 732 | 0.65 |

$^a$TLC on silica gel (Merck) using a water:$CH_3CN$:acetone (1:2:2) solvent system Other N$_{Trp}$-N$_{Orn}$-diacyl derivatives of A-21978C prepared according to the general procedure are listed in Table VI.

TABLE VI

Diacyl Derivatives of A-21978C

| Example No. | R in Formula 1 | R$^1$ in Formula 1 |
|---|---|---|
| 31 | $CH_3(CH_2)_{10}CONH$—⟨phenyl⟩—CO— | $CH_3(CH_2)_{10}CONH$—⟨phenyl⟩—CO— |
| 32 | $CH_3(CH_2)_{10}CONHCHCO$— (indolylmethyl) | t-BOC |
| 33 | $CH_3(CH_2)_{10}CONHCH(CH_2C_6H_5)CO$— | t-BOC |

EXAMPLE 34

Preparation of N$_{Trp}$-[N-(n-Decanoyl)-L-phenylalanyl]-A-21978C Nucleus (Compound of Example 19)

This example illustrates the large-scale preparation of compounds by the active-ester method.

A. Preparation of N-(n-Decanoyl)-L-Phenylalanyl-2,4,5-Trichlorophenolate

A solution of N-(n-decanoyl)-L-phenylalanine (31.9 g, 0.1 mole) and 2,4,5-trichlorophenol (19.7 g, 0.1 mole) in 1 liter of anhydrous ether was treated with N,N'-dicyclohexylcarbodiimide (20.6 g, 0.1 mole). The reaction was stirred overnight at room temperature. The precipitated N,N'-dicyclohexylurea was removed by filtration and discarded. The filtrate was concentrated under vacuum to dryness. The residue obtained was triturated with ether, and the solids (residual cyclohexylurea) were removed by filtration. The filtrate was evaporated to dryness under reduced pressure. The residue was crystallized from acetonitrile to give 36.9 g of crystalline N-(n-decanoyl)-L-phenylalanyl-2,4,5-trichlorophenolate, m.p. 122°–124° C.

B. Preparation of N$_{Trp}$-[N-(N-Decanoyl)-L-phenylalanyl]-N$_{Orn}$-t-BOC-A-21978C Nucleus A solution of N-(n-decanoyl)-L-phenylalanyl-2,4,5-trichlorophenolate (10 g, 0.02 mole), N$_{Orn}$-t-BOC-A-21978C nucleus (10 g, 0.006 mole) in anhydrous DMF (1 L) was stirred at room temperature for 96 hours under an atmosphere of nitrogen. The solvent was removed by evaporation under reduced pressure. The residual material was stirred with a mixture of diethyl ether (800 ml) and chloroform (200 ml) for 2 hours. The product was separated by filtration to give a light brown powder (10.3 g). This material (9.9 g) was dissolved in methanol (200 ml) and purified by preparative HPLC, using a "Prep LC/System 500" unit and a Pre-Pak-500/C$_{18}$ Column as the stationary phase. The column was eluted isocratically, using a water:methanol:acetonitrile (2:1:2) solvent system and collecting 250-ml fractions at a rate of one fraction per minute. The desired compound was eluted in the 9th through the 22nd fractions.

Fractions were combined on the basis of TLC [reversed phase silica gel/C$_{18}$; developed with water:methanol:acetonitrile (3:3:4); detected with Van Urk spray]. Combined fractions were examined by bioautography [silica gel TLC acetonitrile:acetone:water (2:2:1) solvent system and *Micrococcus luteus* as the detecting organism] and were shown to consist of a single bioactive component. This procedure gave 6.02 g of N$_{Trp}$-[N-(n-decanoyl)-L-phenylalanyl]-N$_{Orn}$-t-BOC-A-21978C nucleus [compound of formula 1: R=N-(n-decanoyl)-L-phenylalanyl); R$^1$=t-BOC].

C. Preparation of N$_{Trp}$-[N-(n-Decanoyl)-L-phenylalanyl]-A-21978C Nucleus A flask (100 ml) was cooled to 5° C. in an icebath. N$_{Trp}$-[N-(n-decanoyl)-L-phenylalanyl]-N$_{Orn}$-t-BOC-A-21978C nucleus (6.02 g, 0.008 mole), prepared as described in Section B, and then anhydrous trifluoroacetic acid containing 2% anisole (50 ml) were added to the flask. The mixture, which went into solution in approximately two minutes, was stirred under an atmosphere of nitrogen for ten minutes. The solution was evaporated to dryness under reduced pressure at below 40° C. to give a gummy solid which was triturated twice with a diethyl ether:dichloromethane (4:1) solution (two 100-ml volumes). The solids were collected by filtration and washed with diethyl ether to give the TFA salt. This was dissoled in water (50 ml), and the pH of the solution was adjusted to 5.4 with pyridine. The solution was then lyophilized to give 6.1 g of off-white lyophilizate.

The lyophilizate, dissolved in methanol (35 ml), was purified using a reverse-phase C$_{18}$ silica-gel column (Waters Associates, Prep 500), eluting in stepwise gradient with H$_2$O:CH$_3$OH:CH$_3$CN containing 0.1% pyridinium acetate at ratios of 3:1:2, 2:1:2 and 1:2:2 and collecting fractions having a volume of 250 ml. The desired product was eluted during the 2:1:2 elution. The fractions containing the product were lyophilized to give 2.23 g of cream-colored N$_{Trp}$-[N-(n-decanoyl)-L-phenylalanyl]-A-21978C nucleus (compound of formula 1: R=N-(n-decanoyl)-L-phenylalanyl; R$^1$=H).

The product was evaluated by analytical HPLC [reversed-phase C$_{18}$ silica-gel column, MeOH:CH$_3$CN:H$_2$O:PyOAc (15:35:49:1) solvent and UV detection at 230 nm], by TLC [reversed-phase C$_{18}$ silica-gel plates (Whatman), H$_2$O:CH$_3$OH:CH$_3$CN (3:3:4) solvent and Van Urk spray and short-wave UV for detection] and by bioautography [silica-gel TLC (Merck), an H$_2$O:CH$_3$CN:acetone (1:2:2) solvent, and *Micrococcus luteus* as the detecting organism]. Each of these methods demonstrated that the product was homogenous. Substitution at the tryptophan N-terminus position was confirmed by 360 MHz PMR. Amino-acid analysis confirmed the incorporation of one equivalent of L-phenylalanine into the product.

EXAMPLE 34

The antibacterial activity of the compounds of formula 1 can be demonstrated in vitro, using standard agar-dilution tests. The results of the antibacterial testing of representative compounds of formula 1 are set forth in Table VII. In Table VII activity is measured by the minimal inhibitory concentration (MIC), i.e. the lowest concentration of compound at which growth of the microorganism is inhibited by the test compound.

TABLE VII

| | Antibiotic Activity of A-21978C Cyclic Peptides | | | | | | | | | |
|---|---|---|---|---|---|---|---|---|---|---|
| Test Organism | MIC$^a$ of Test Compound$^b$ | | | | | | | | | |
| | 1 | 2$^e$ | 3 | 4$^f$ | 5 | 6 | 7 | 8 | 9$^f$ | 10$^f$ | 11 |
| *Staphylococcus aureus* X1.1 | 0.5 | 4 | 2 | 4,8 | 0.5 | 1 | 0.5 | 0.25 | 32,64 | 0.5,0.25 | 0.5 |
| *Staphylococcus aureus* V41$^c$ | 0.5 | 4 | 2 | 4,16 | 0.5 | 2 | 1 | 0.25 | 64,128 | 0.5,0.5 | 0.25 |
| *Staphylococcus aureus* X400$^d$ | 1 | 4 | 8 | 8,16 | 1 | 4 | 2 | 0.5 | 64,128 | 1,0.5 | 2 |
| *Staphylococcus aureus* S13E | 0.5 | 4 | 2 | 4,8 | 0.5 | 2 | 0.5 | 0.25 | 32,64 | 0.5,0.5 | 0.5 |
| *Staphylococcus epidermidis* EPI1 | 2 | 4 | 8 | 16,64 | 2 | 2 | 2 | 1 | 128,>128 | 2,1 | 0.5 |
| *Staphylococcus epidermidis* EPI2 | 1 | 2 | 8 | 16,64 | 1 | 2 | 2 | 1 | 128,>128 | 1,0.5 | 0.5 |
| *Streptococcus pyogenes* C203 | 0.125 | 1 | 2 | 4,8 | 0.25 | 0.5 | 1 | 0.25 | 16,16 | 0.125,0.06 | 0.125 |
| *Streptococcus pneumoniae* Park I | 0.125 | 4 | 0.5 | 4,16 | 0.25 | 2 | 0.125 | 0.125 | 32,64 | 0.25,0.25 | 0.06 |
| *Streptococcus* Group D X66 | 1 | 32 | 8 | 32,>64 | 4 | 16 | 2 | 1 | >128,>128 | 4,4 | 2 |
| *Streptococcus* Group D 9960 | 0.5 | 8 | 8 | 8,32 | 1 | 2 | 2 | 0.25 | 128,>128 | 2,1 | 4 |
| | 12 | 13 | 14 | 15 | 16 | 17 | 18 | 19$^g$ | 20 | 21 | 22 |
| *Staphylococcus aureus* X1.1 | 1 | 0.25 | 4 | 1 | 0.5 | 4 | 2 | 0.5 | 0.5 | 0.5 | 0.5 |
| *Staphylococcus aureus* V41$^c$ | 2 | 0.25 | 4 | 2 | 0.5 | 8 | 2 | 0.5 | 0.5 | 0.5 | 1 |

TABLE VII-continued
Antibiotic Activity of A-21978C Cyclic Peptides

| Test Organism | MIC[a] of Test Compound[b] | | | | | | | | | | |
|---|---|---|---|---|---|---|---|---|---|---|---|
| Staphylococcus aureus X400[d] | 4 | 0.5 | 8 | 8 | 1 | 8 | 4 | 1 | 2 | 2 | 2 |
| Staphylococcus aureus S13E | 2 | 0.25 | 4 | 2 | 0.5 | 8 | 2 | 0.5 | 0.5 | 0.5 | 1 |
| Staphylococcus epidermidis EPI1 | 4 | 0.5 | 8 | 4 | 1 | 8 | 4 | 1 | 2 | 2 | 4 |
| Staphylococcus epidermidis EPI2 | 4 | 0.25 | 8 | 4 | 1 | 8 | 2 | 0.5 | 2 | 2 | 4 |
| Streptococcus pyogenes C203 | 2 | 0.03 | 2 | 1 | 0.5 | 2 | 0.5 | 0.25 | 0.125 | 0.125 | 0.25 |
| Streptococcus pneumoniae Park I | 1 | 0.03 | 8 | 0.25 | 0.125 | — | — | 0.75 | — | — | — |
| Streptococcus Group D X66 | 16 | 1 | >128 | 4 | 1 | 128 | 32 | 8 | 4 | 1 | 1 |
| Streptococcus Group D 9960 | 4 | 0.25 | 64 | 4 | 0.5 | 32 | 8 | 2 | 2 | 0.25 | 0.5 |

| | 23 | 24 | 25 | 26 | 27 | 28 | 29[f] | 30 | 31[f] | 32 | 33 |
|---|---|---|---|---|---|---|---|---|---|---|---|
| Staphylococcus aureus X1.1 | 0.5 | 1 | 8 | 8 | 0.5 | 0.5 | 0.5,1 | 1 | 16,2 | 1 | 0.5 |
| Staphylococcus aureus V41[c] | 1 | 2 | 16 | >128 | 2 | 2 | 4,4 | 1 | 32,4 | 1 | 2 |
| Staphylococcus aureus X400[d] | 4 | 4 | 16 | >128 | 1 | 1 | 1,1 | 2 | 32,8 | 2 | 2 |
| Staphylococcus aureus S13E | 1 | 2 | 8 | 16 | 0.5 | 0.5 | 0.5,1 | 1 | 16,4 | 1 | 1 |
| Staphylococcus epidermidis EPI1 | 2 | 4 | 16 | >128 | 4 | 4 | 8,16 | 2 | 128,16 | 4 | 8 |
| Staphylococcus epidermidis EPI2 | 2 | 4 | 16 | >128 | 4 | 4 | 8,16 | 1 | 64,8 | 4 | 8 |
| Streptococcus pyogenes C203 | 0.25 | 2 | 4 | 1 | 0.5 | 0.5 | 1,0.5 | 0.25 | 8,4 | 1 | 1 |
| Streptococcus pneumoniae Park I | 0.25 | 1 | 8 | — | 0.5 | 0.25 | 0.25,0.5 | 0.25 | 8,4 | 0.5 | 0.5 |
| Streptococcus Group D X66 | 4 | 16 | 128 | >128 | 8 | 4 | 8,16 | 64 | >128, 32 | 8 | 16 |
| Streptococcus Group D 9960 | 2 | 4 | 32 | 32 | 4 | 4 | 32,32 | 32 | 64,8 | 4 | 4 |

[a] MIC in mcg/ml
[b] Compound numbers = example numbers in Tables III-VI
[c] Penicillin-resistant strain
[d] Methicillin-resistant-strain
[e] Median of five experiments
[f] Two experiments
[g] Median of three experiments The A-21978C cyclic peptides of formula 1 have shown in vivo antimicrobial activity against experimental bacterial infections. When two doses of test compound were administered subcutaneously or orally to mice in illustrative infections, the activity observed was measured as an $ED_{50}$ value [effective dose in mg/kg to protect fifty percent of the test animals: See Warren Wick, et al., *J. Bacteriol.* 81, 233-235 (1961)]. The $ED_{50}$ values observed for A-21978C compounds are given in Tables VIII and IX.

TABLE VIII
In Vivo Activity of A-21978C Cyclic Peptides

| Compound No. | Formula 1 Compound[a] R | $ED_{50}$ Values[b] | | |
|---|---|---|---|---|
| | | Staphylococcus aureus Subcutaneous | Streptococcus pyogenes Subcutaneous | Oral |
| 1 | (D)CH$_3$(CH$_2$)$_{10}$CONHCH(CH$_2$C$_6$H$_5$)CO— | 1.4, 2.05[c] | <0.25, 0.21 | >200 |
| 2 | CH$_3$(CH$_2$)$_{10}$CONH(CH$_2$)$_4$—CO— | 0.65, 0.93 | <0.25, 0.107 | 117 |
| 3 | CH$_3$(CH$_2$)$_{10}$CONH(CH$_2$)$_{10}$—CO— | >18 | 6.2 | >200 |
| 4 | 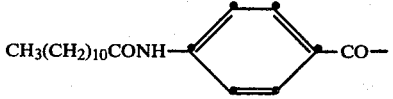 | <5 | 18.8 | >200 |
| 5 | 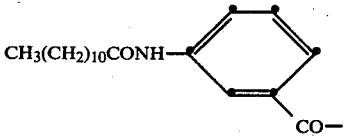 | 1.67 | >0.25, 0.46 | >200 |
| 7 | 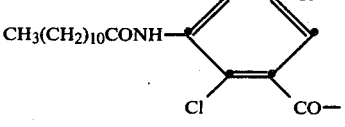 | 19 | 0.23 | >200 |
| 8 | (L)CH$_3$(CH$_2$)$_{10}$CONHCH(CH$_2$C$_6$H$_5$)CO— | 2.35 | 0.32 | 150 |
| 10 | 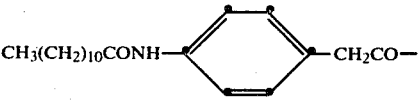 | 3.56, 4.12[c] | 0.69 | >200 |

TABLE VIII-continued

In Vivo Activity of A-21978C Cyclic Peptides

| Compound No. | Formula 1 Compound[a] R | $ED_{50}$ Values[b] Staphylococcus aureus Subcutaneous | Streptococcus pyogenes Subcutaneous | Oral |
|---|---|---|---|---|
| 11 | $CH_3(CH_2)_{10}CONH$—⬡—$CH=CH$—$CO$— | 0.65 | 0.04 | 59 |
| 12 | $CH_3(CH_2)_{10}CONH$—⬡—$CONHCH_2$—$CO$— | 2.3 | <0.25, 0.12[c] | >200 |
| 13 | $CH_3(CH_2)_{10}CONH$—(pyridyl)—$CO$— | 0.54 | 0.05 | 69 |
| 14 | $CH_3(CH_2)_5CONH(CH_2)_{10}$—$CO$— | >18 | >9 | >200 |
| 15 | $CH_3(CH_2)_{12}CONH$—⬡—$CO$— | >18 | 1.02 | >200 |
| 16 | (L)-$CH_3(CH_2)_{10}CONH$—$CH$—$CO$— (indolyl) | 5.19 | 3.14 | 200 |
| 17 | (L)$CH_3(CH_2)_6CONHCH(CH_2C_6H_5)CO$— | 2.58 | 1.48 | >200 |
| 18 | (L)$CH_3(CH_2)_7CONHCH(CH_2C_6H_5)CO$— | 1.38 | 0.59 | 184 |
| 19 | (L)$CH_3(CH_2)_8CONHCH(CH_2C_6H_5)CO$— | 0.7, 0.98[c] | 0.39 | >200 |
| 20 | (L)$CH_3(CH_2)_9CONHCH(CH_2C_6H_5)CO$— | 1.25 | 0.35 | >200 |
| 21 | (L)$CH_3(CH_2)_{11}CONHCH(CH_2C_6H_5)CO$— | 0.76 | 0.14 | >200 |
| 22 | (L)$CH_3(CH_2)_{12}CONHCH(CH_2C_6H_5)CO$— | 4.8 | <0.27, 0.36[c] | >200 |
| 24 | $CH_3(CH_2)_{10}CONH$—⬡—$CONHCH_2CO$— | 2.3 | <0.25, 0.12[c] | >200 |

[a] $R^1 = H$
[b] mg/kg × 2
[c] Two experiments

TABLE IX

In Vivo Activity of A-21978C Cyclic Peptides

| Compound No. | R | Formula 1 Compound $R^1$ | $ED_{50}$ Values[a] Staphylococcus aureus Subcutaneous | Streptococcus pyogenes Subcutaneous | Oral |
|---|---|---|---|---|---|
| 25 | H | $CH_3(CH_2)_{10}CONH$—⬡—$CO$— | >70 | >22 | >200 |
| 26 | H | $CH_3(CH_2)_9CONHCH(CH_2C_6H_5)CO$— | 9.2 | >18 | >200 |

TABLE IX-continued

In Vivo Activity of A-21978C Cyclic Peptides

| Compound No. | Formula 1 Compound R | R[1] | ED$_{50}$ Values[a] Staphylococcus aureus Subcutaneous | Streptococcus pyogenes Subcutaneous | Oral |
|---|---|---|---|---|---|
| 29 | $CH_3CH_2CH(CH_3)(CH_2)_8CO-$ | (L)-$CH_3(CH_2)_4CONHCH-CO-$ 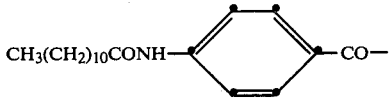 | >2.2, >70[b] | 10.6, 6.0 | >200 |

[a] mg/kg × 2
[b] Two experiments

The results of toxicity tests on some of the A-21978C cyclic peptides are summarized in Table X.

TABLE X

Toxicity of A-21978C Cyclic Peptides

| Compound No. | Formula 1 Compound R | R[1] | LD$_{50}$ (mg/kg) in Mice[a] |
|---|---|---|---|
| 1 | (D)$CH_3(CH_2)_{10}CONHCH(CH_2C_6H_5)CO-$ | H | 250 |
| 2 | $CH_3(CH_2)_{10}CONH(CH_2)_4-CO-$ | H | >600 |
| 3 | $CH_3(CH_2)_{10}CONH(CH_2)_{10}-CO-$ | H | 600 |
| 4 | $CH_3(CH_2)_{10}CONH-$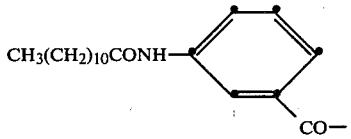$-CO-$ | H | >300 |
| 5 | $CH_3(CH_2)_{10}CONH-$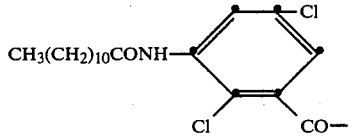$-CO-$ | H | 277 |
| 7 | $CH_3(CH_2)_{10}CONH-$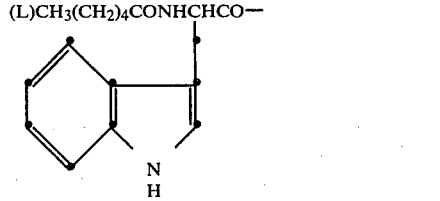 (Cl, Cl substituents) $-CO-$ | H | 200 |
| 8 | (L)$CH_3(CH_2)_{10}CONHCH(CH_2C_6H_5)CO-$ | H | 250 |
| 9 | (L)$CH_3(CH_2)_4CONHCHCO-$ 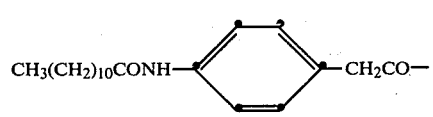 | H | 450[b] |
| 10 | $CH_3(CH_2)_{10}CONH-$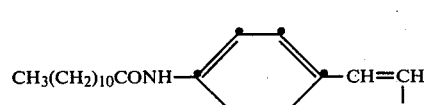$-CH_2CO-$ | H | 450 |
| 11 | $CH_3(CH_2)_{10}CONH-$ —CH=CH—CO— | H | 450 |

TABLE X-continued
Toxicity of A-21978C Cyclic Peptides

| Compound No. | R (Formula 1 Compound) | R¹ | LD$_{50}$ (mg/kg) in Mice[a] |
|---|---|---|---|
| 12 | CH$_3$(CH$_2$)$_{10}$CONH—⟨benzene⟩—CONHCH$_2$CO— | H | 450 |
| 13 | CH$_3$(CH$_2$)$_{10}$CONH—⟨pyridine⟩—CO— | H | 300 |
| 14 | CH$_3$(CH$_2$)$_5$CONH(CH$_2$)$_{10}$—CO— | H | >600 |
| 15 | CH$_3$(CH$_2$)$_{12}$CONH—⟨benzene⟩—CO— | H | 250 |
| 16 | (L)-CH$_3$(CH$_2$)$_{10}$CONH—CH—CO— (with indole side chain) | H | 225 |
| 17 | (L)CH$_3$(CH$_2$)$_6$CONHCH(CH$_2$C$_6$H$_5$)CO— | H | 450 |
| 18 | (L)CH$_3$(CH$_2$)$_7$CONHCH(CH$_2$C$_6$H$_5$)CO— | H | >600 |
| 19 | (L)CH$_3$(CH$_2$)$_8$CONHCH(CH$_2$C$_6$H$_5$)CO— | H | 600 |
| 20 | (L)CH$_3$(CH$_2$)$_9$CONHCH(CH$_2$C$_6$H$_5$)CO— | H | 400 |
| 21 | (L)CH$_3$(CH$_2$)$_{11}$CONHCH(CH$_2$C$_6$H$_5$)CO— | H | 225 |
| 22 | (L)CH$_3$(CH$_2$)$_{12}$CONHCH(CH$_2$C$_6$H$_5$)CO— | H | 225 |
| 24 | CH$_3$(CH$_2$)$_{10}$CONH—⟨benzene⟩—CONHCH$_2$CO— | H | 450 |
| 25 | H | CH$_3$(CH$_2$)$_{10}$CONH—⟨benzene⟩—CO— | 300 |
| 26 | H | CH$_3$(CH$_2$)$_9$CONHCH(CH$_2$C$_6$H$_5$)CO— | 225 |
| 29 | CH$_3$CH$_2$CH(CH$_3$)(CH$_2$)$_8$CO— | (L)-CH$_3$(CH$_2$)$_4$CONHCH—CO— (with indole side chain) | 37.5 |

[a]Administered intravenously
[b]Material was in suspension

I claim:
1. An A-21978C cyclic peptide derivative of the formula:

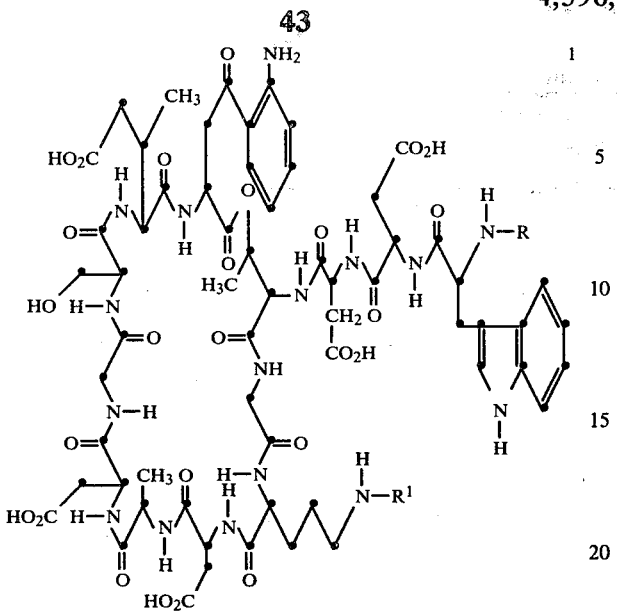

wherein R is hydrogen, 8-methyldecanoyl, 10-methyldodecanoyl, 10-methylundecanoyl, the specific $C_{10}$-alkanoyl group of A-21978$C_0$ or the specific $C_{12}$-alkanoyl groups of A-21978C factors $C_4$ and $C_5$, an amino-protecting group, an aminoacyl group of the formula

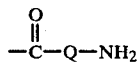

wherein Q is $C_1$–$C_{16}$ alkylene, or an N-alkanoylamino acyl group of the formula

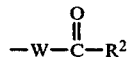

wherein:

W is a divalent aminoacyl radical of the formula:

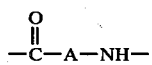 (a)

wherein A is $C_1$–$C_{10}$ alkylene or $C_5$–$C_6$ cycloalkylene;

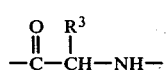 (b)

wherein $R^3$ is hydroxymethyl, hydroxyethyl, mercaptomethyl, mercaptoethyl, methylthioethyl, 2-thienyl, 3-indole-methyl, phenyl, benzyl, or substituted phenyl or substituted benzyl in which the benzene ring thereof is substituted with chloro, bromo, iodo, nitro, $C_1$–$C_3$ alkyl, hydroxy, $C_1$–$C_3$-alkoxy, $C_1$–$C_3$ alkylthio, carbamyl, or $C_1$–$C_3$ alkylcarbamyl;

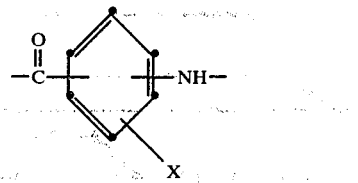 (c)

wherein X is hydrogen chloro, bromo, iodo, amino, nitro, $C_1$–$C_3$ alkyl, hydroxy, $C_1$–$C_3$ alkoxy, mercapto, $C_1$–$C_3$ alkylthio, carbamyl, or $C_1$–$C_3$ alkylcarbamyl;

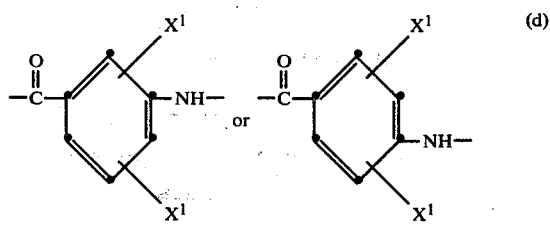 (d)

wherein $X^1$ is chloro, bromo, iodo, amino, hydroxy, $C_1$–$C_3$ alkyl or $C_1$–$C_3$ alkoxy;

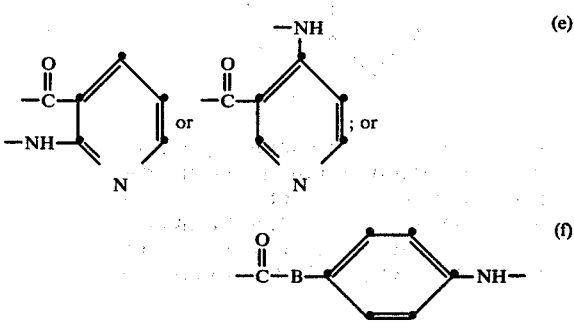 (e)

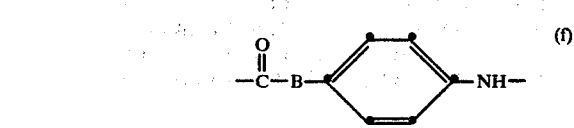

 (f)

wherein B is a divalent radical of the formula: —(CH$_2$)$_n$— and n is an integer from 1 to 3; —CH=CH—; —CH=CH—CH$_2$—; or

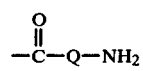

$R^2$ is $C_1$–$C_{17}$ alkyl or $C_2$–$C_{17}$ alkenyl; and
$R^1$ is hydrogen, an amino-protecting group, an aminoacyl group of the formula

as herein defined, or an N-alkanoylaminoacyl group of the formula

—W—C(=O)—R$^2$ as herein defined; provided that, when R is other than aminoacyl or N-alkanoylaminoacyl, $R^1$ must be aminoacyl or N-alkanoylaminoacyl; and, when $R^1$ is an amino-protecting group, R must be aminoacyl or N-alkanoylaminoacyl; and the salts thereof.

2. A compound of claim 1 wherein R is

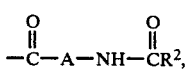
$$-\overset{O}{\underset{\|}{C}}-A-NH-\overset{O}{\underset{\|}{C}}R^2,$$

A is $C_1$-$C_{10}$ alkylene and $R^2$ is straight chain $C_1$-$C_{17}$ alkyl.

3. A compound of claim 2 wherein $R^1$ is hydrogen.

4. The compound of claim 3 wherein R is 5-[N-(n-dodecanoyl)amino]-n-pentanoyl.

5. The compound of claim 3 wherein R is 11-[N-(n-dodecanoyl)amino]-n-undecanoyl.

6. The compound of claim 3 wherein R is 11-[N-(n-heptanoyl)amino]-n-undecanoyl.

7. A compound of claim 1 wherein R is

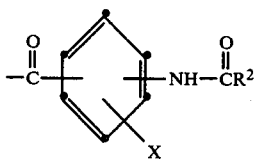

X is hydrogen and $R_2$ is straight chain $C_1$-$C_{17}$ alkyl.

8. A compound of claim 7 wherein $R^1$ is hydrogen.

9. The compound of claim 8 wherein R is p-[N-(n-dodecanoyl)amino]benzoyl.

10. The compound of claim 8 wherein R is m-[N-(n-dodecanoyl)amino]benzoyl.

11. The compound of claim 8 wherein R is p-[N-(n-tetradecanoyl)amino]benzoyl.

12. A compound of claim 1 wherein R is

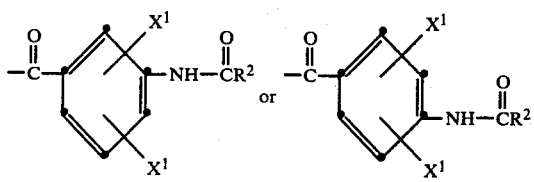

$X^1$ is chloro, bromo, iodo, amino, $C_1$-$C_3$ alkyl, hydroxy, or $C_1$-$C_3$ alkoxy, and $R^2$ is straight chain $C_1$-$C_{17}$ alkyl.

13. A compound of claim 12 wherein $R^1$ is hydrogen.

14. The compound of claim 13 wherein R is 5-amino-4-[N-(n-dodecanoyl)amino]-2-hydroxybenzoyl.

15. The compound as defined in claim 13 wherein R is 3-[N-(n-dodecanoyl)amino]-2,5-dichlorobenzoyl.

16. The compound of claim 1 wherein R is p-[N-(n-dodecanoyl)amino]phenylacetyl and $R^1$ is hydrogen.

17. The compound of claim 1 wherein R is p-[N-(n-dodecanoyl)amino]cinnamoyl and $R^1$ is hydrogen.

18. The compound of claim 1 wherein R is p-[N-(n-dodecanoyl)amino]hippuryl and $R^1$ is hydrogen.

19. The compound of claim wherein R is 2-[N-(n-dodecanoyl)amino]nicotinoyl and $R^1$ is hydrogen.

20. A compound of claim 1 wherein R is

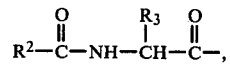
$$R^2-\overset{O}{\underset{\|}{C}}-NH-\overset{R_3}{\underset{|}{CH}}-\overset{O}{\underset{\|}{C}}-,$$

$R^2$ is $C_1$-$C_{17}$alkyl and $R^3$ is phenyl, benzyl or 3-indolemethyl.

21. A compound of claim 20 wherein $R^1$ is hydrogen.

22. The compound of claim 21 wherein R is N-(n-dodecanoyl)phenylalanyl.

23. The compound of claim 21 wherein R is N-(n-octanoyl)phenylalanyl.

24. The compound of claim 21 wherein R is N-(n-nonanoyl)phenylalanyl.

25. The compound of claim 21 wherein R is N-(n-decanoyl)phenylalanyl.

26. The compound of claim 21 wherein R is N-(n-undecanoyl)phenylalanyl.

27. The compound of claim 21 wherein R is N-(n-tridecanoyl)phenylalanyl.

28. The compound of claim 21 wherein R is N-(n-tetradecanoyl)phenylalanyl.

29. The compound of claim 21 wherein R is N-(n-hexanoyl)tryptophanyl.

30. The compound of claim 21 wherein R is N-(n-dodecanoyl)tryptophanyl.

31. A compound of claim 20 wherein R is N-(n-hexanoyl)tryptophanyl.

32. The compound of claim 31 wherein $R^1$ is 8-methyldecanoyl.

33. The compound of claim 31 wherein $R^1$ is 10-methyldodecanoyl.

34. The compound of claim 31 wherein $R^1$ is 10-methylundecanoyl.

* * * * *